United States Patent
Muse et al.

(10) Patent No.: US 12,283,129 B2
(45) Date of Patent: Apr. 22, 2025

(54) MOVEMENT PREDICTION MACHINE LEARNING MODELS

(71) Applicant: UnitedHealth Group Incorporated, Minnetonka, MN (US)

(72) Inventors: Jon Kevin Muse, Thompsons Station, TN (US); Rama S. Ravindranathan, Edison, NJ (US); Marilyn L. Gordon, Cherry Hill, NJ (US); Gregory J. Boss, Saginaw, MI (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 381 days.

(21) Appl. No.: 17/453,059

(22) Filed: Nov. 1, 2021

(65) Prior Publication Data

US 2023/0133858 A1   May 4, 2023

(51) Int. Cl.
*G06V 40/20* (2022.01)
*G06F 1/16* (2006.01)
*G06N 20/00* (2019.01)

(52) U.S. Cl.
CPC .............. *G06V 40/25* (2022.01); *G06F 1/163* (2013.01); *G06N 20/00* (2019.01)

(58) Field of Classification Search
CPC .......... G06V 40/20; G06V 40/25; G06F 1/16; G06F 1/163; G06N 20/00; G06N 3/08; A61N 1/36; A61N 1/3603; A61N 1/04; A61N 1/0456; A61N 1/0484; A61N 1/36003; A61N 1/36031; G16H 10/20; G16H 10/60; G16H 20/30; G16H 40/40; G16H 40/63; G16H 40/67; G16H 50/20; G16H 50/70
See application file for complete search history.

(56) References Cited

U.S. PATENT DOCUMENTS

| | | | |
|---|---|---|---|
| 7,526,954 B2 | 5/2009 | Haselhurst et al. | |
| 8,936,560 B2 * | 1/2015 | Lunau | A61F 5/0123 602/2 |
| 8,972,017 B2 | 3/2015 | Dar et al. | |
| 9,452,101 B2 | 9/2016 | Tomlinson et al. | |

(Continued)

FOREIGN PATENT DOCUMENTS

| | | | | |
|---|---|---|---|---|
| CN | 103518171 A | * | 1/2014 | ............. G06F 3/016 |
| CN | 108831527 B | * | 6/2021 | ............ A61B 5/1118 |

OTHER PUBLICATIONS

"Post-Stroke Rehabilitation Fact Sheet," National Institute of Neurological Disorders and Stroke, Apr. 2020, (10 pages), (article, online), [Retrieved from the Internet Feb. 21, 2022] <URL: https://www.ninds.nih.gov/Disorders/Patient-Caregiver-Education/Fact-Sheets/Post-Stroke-Rehabilitation-Fact-Sheet>.

(Continued)

*Primary Examiner* — Edward F Urban
*Assistant Examiner* — Benedict E Lee
(74) *Attorney, Agent, or Firm* — Alston & Bird LLP

(57) ABSTRACT

Various embodiments of the present disclosure provide methods, apparatuses, systems, computing devices, computing entities, and/or the like for monitoring a user's movement in real-time and providing or augmenting stimulation. For example, various embodiments provide techniques generating movement prediction profiles using movement prediction machine learning models and for use in conjunction with wearable devices.

20 Claims, 11 Drawing Sheets

(56) References Cited

U.S. PATENT DOCUMENTS

| | | |
|---|---|---|
| 9,597,497 B2 | 3/2017 | Swain et al. |
| 11,948,470 B2* | 4/2024 | Statham ................ A61B 5/486 |
| 2007/0203435 A1 | 8/2007 | Novak |
| 2007/0203533 A1 | 8/2007 | Goren et al. |
| 2019/0009133 A1* | 1/2019 | Mettler May ...... G09B 19/0038 |
| 2019/0105217 A1 | 4/2019 | Prattichizzo et al. |
| 2020/0139118 A1* | 5/2020 | John .................... A61N 5/0613 |
| 2020/0152078 A1* | 5/2020 | Caban .................. G05B 13/028 |
| 2020/0330022 A1 | 10/2020 | Oddsson et al. |
| 2020/0367823 A1* | 11/2020 | Chahine ................ A41B 11/00 |
| 2021/0086024 A1* | 3/2021 | McCarthy .............. G16H 50/30 |
| 2022/0176545 A1* | 6/2022 | Robison ............... A61B 5/1038 |

OTHER PUBLICATIONS

"Pressure Offloading & Foot Function," Tekscan, (11 pages), (article), Available online: https://www.tekscan.com/products-solutions/pressure-offloading-foot-function.

"Walkasins Device|Help For Peripheral Neuropathy In Feet," RxFunction, (6 pages), (article, online), [Retrieved from the Internet Jul. 22, 2021] <URL: https://rxfunction.com/our-product/>.

Wikipedia Contributors. "Electroactive Polymer," Wikipedia, The Free Encyclopedia, Dec. 21, 2021, (11 pages), Available online: https://en.wikipedia.org/w/index.php?title=Electroactive_polymer&oldid=1061319993.

* cited by examiner

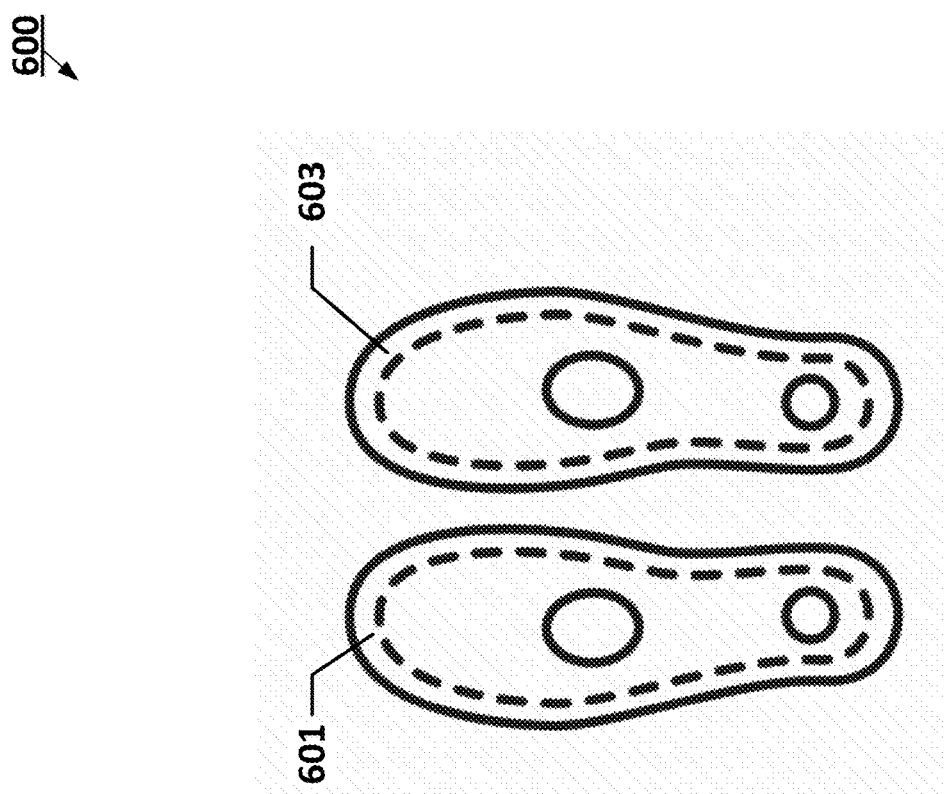

MOVEMENT PREDICTION MACHINE LEARNING MODELS

BACKGROUND

Various individuals may experience reduced mobility as a result of nervous system related conditions and/or nerve damage. Through applied effort, ingenuity, and innovation, various apparatuses, systems, and methods have been realized for monitoring a user's movement in real-time and providing or augmenting stimulation to assist with increased mobility.

BRIEF SUMMARY

In general, various embodiments of the present disclosure provide methods, apparatuses, systems, computing devices, computing entities, and/or the like for monitoring a user's movements and providing nervous system stimulation/feedback in real-time that utilize movement prediction machine learning models.

In accordance with one aspect, a method is provided. In one embodiment, the method comprises: identifying, by the one or more processors and based at least in part on the event data object, one or more movement characteristics associated with a user; determining, by the one or more processors, based at least in part on the one or more movement characteristics and using a movement prediction machine learning model, the movement prediction profile, wherein: (i) the event data object comprises sensor data describing user movement information, (ii) the movement prediction profile comprises a plurality of movement feature sets associated with at least one foot of the user, (ii) each movement feature set is associated with a stimulation protocol, and (iv) each stimulation protocol is associated with one or more target foot zones; and performing, by the one or more processors, one or more prediction-based tasks based at least in part on the movement prediction profile.

In accordance with another aspect, a computer program product is provided. The computer program product may comprise at least one computer-readable storage medium having computer-readable program code portions stored therein, the computer-readable program code portions comprising executable portions configured to: identify, based at least in part on the event data object, one or more movement characteristics associated with a user; determine, based at least in part on the one or more movement characteristics and using a movement prediction machine learning model, the movement prediction profile, wherein: (i) the event data object comprises sensor data describing user movement information, (ii) the movement prediction profile comprises a plurality of movement feature sets associated with at least one foot of the user, (ii) each movement feature set is associated with a stimulation protocol, and (iv) each stimulation protocol is associated with one or more target foot zones; and perform one or more prediction-based tasks based at least in part on the movement prediction profile.

In accordance with yet another aspect, an apparatus comprising at least one processor and at least one memory including computer program code is provided. In one embodiment, the at least one memory and the computer program code may be configured to, with the processor, cause the apparatus to: identify, based at least in part on the event data object, one or more movement characteristics associated with a user; determine, based at least in part on the one or more movement characteristics and using a movement prediction machine learning model, the movement prediction profile, wherein: (i) the event data object comprises sensor data describing user movement information, (ii) the movement prediction profile comprises a plurality of movement feature sets associated with at least one foot of the user, (ii) each movement feature set is associated with a stimulation protocol, and (iv) each stimulation protocol is associated with one or more target foot zones; and perform one or more prediction-based tasks based at least in part on the movement prediction profile.

BRIEF DESCRIPTION OF THE DRAWINGS

Figure 1:
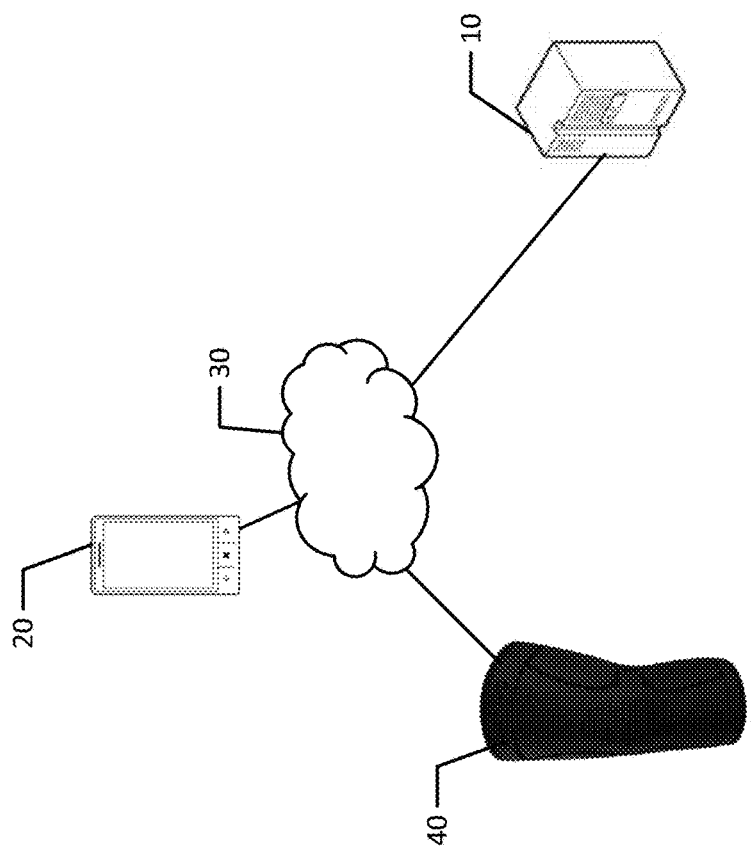
Figure 2:
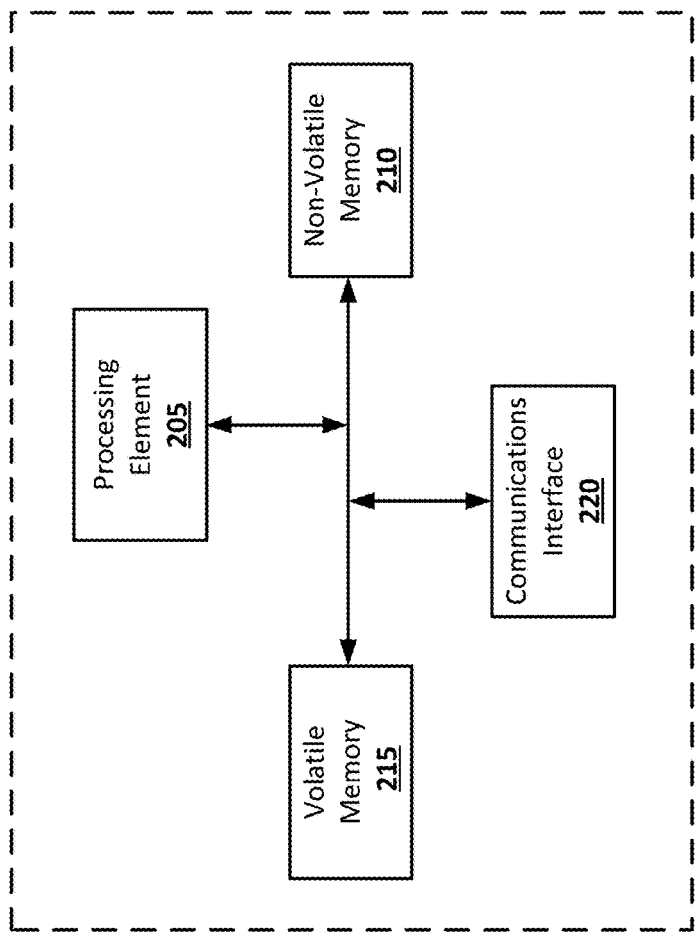
Figure 3:
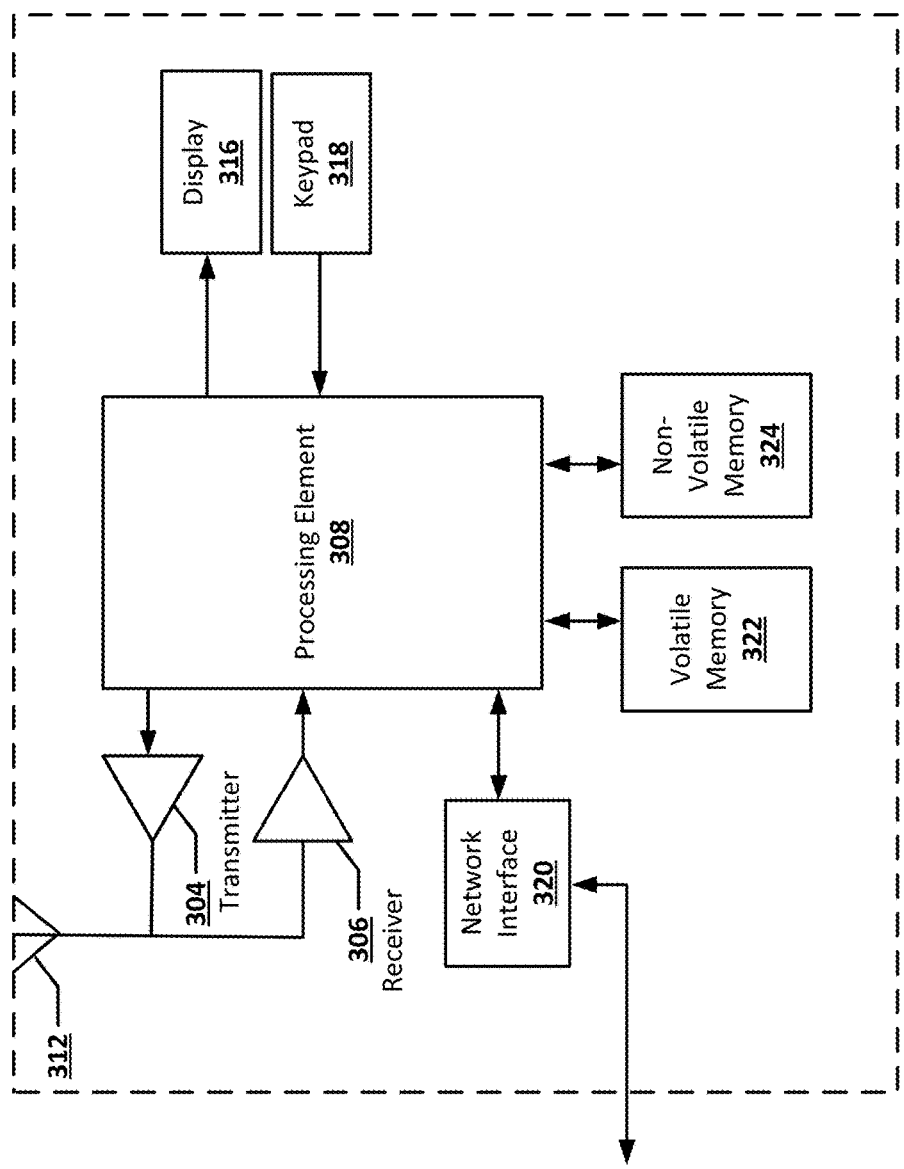
Figure 4:
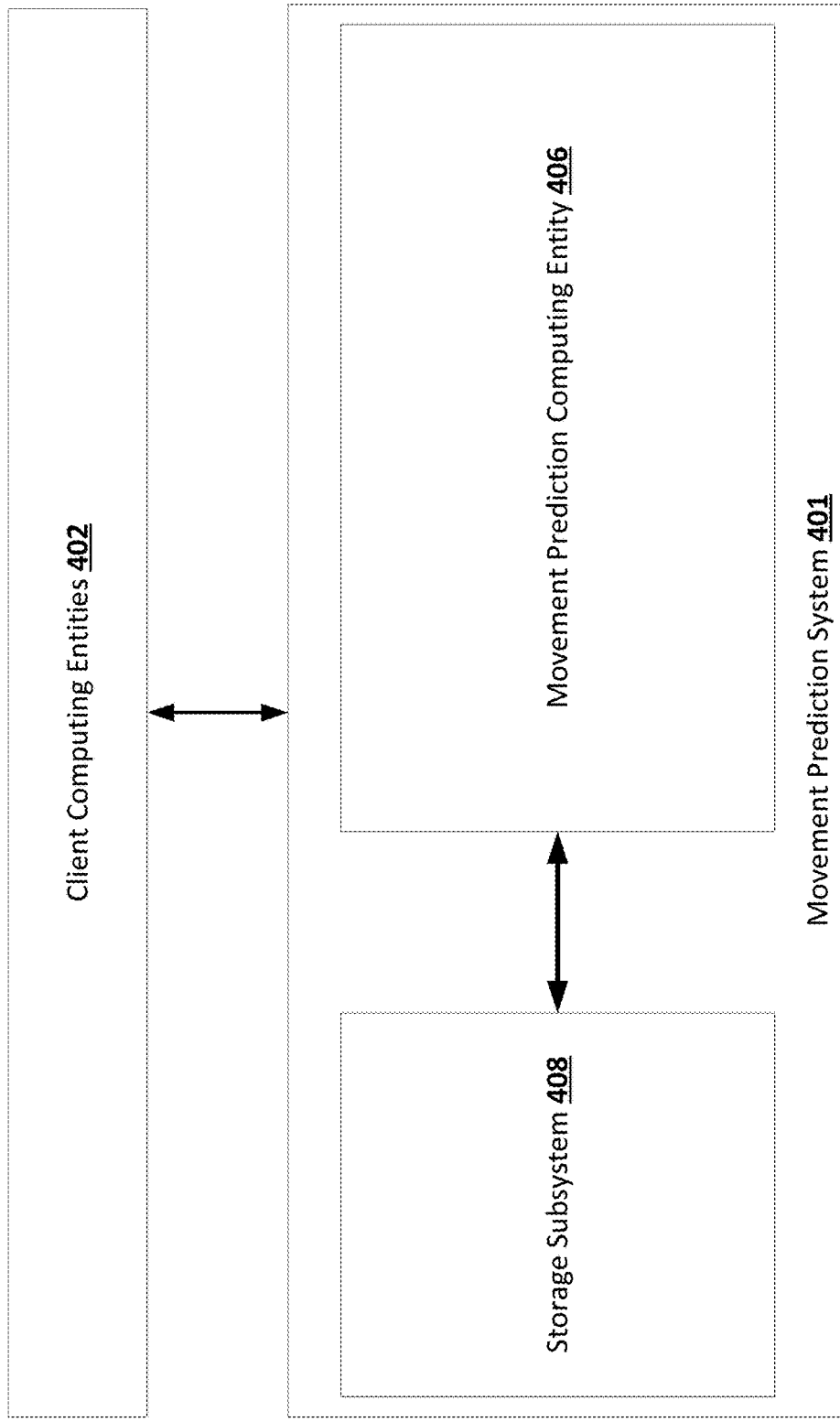
Figure 5:
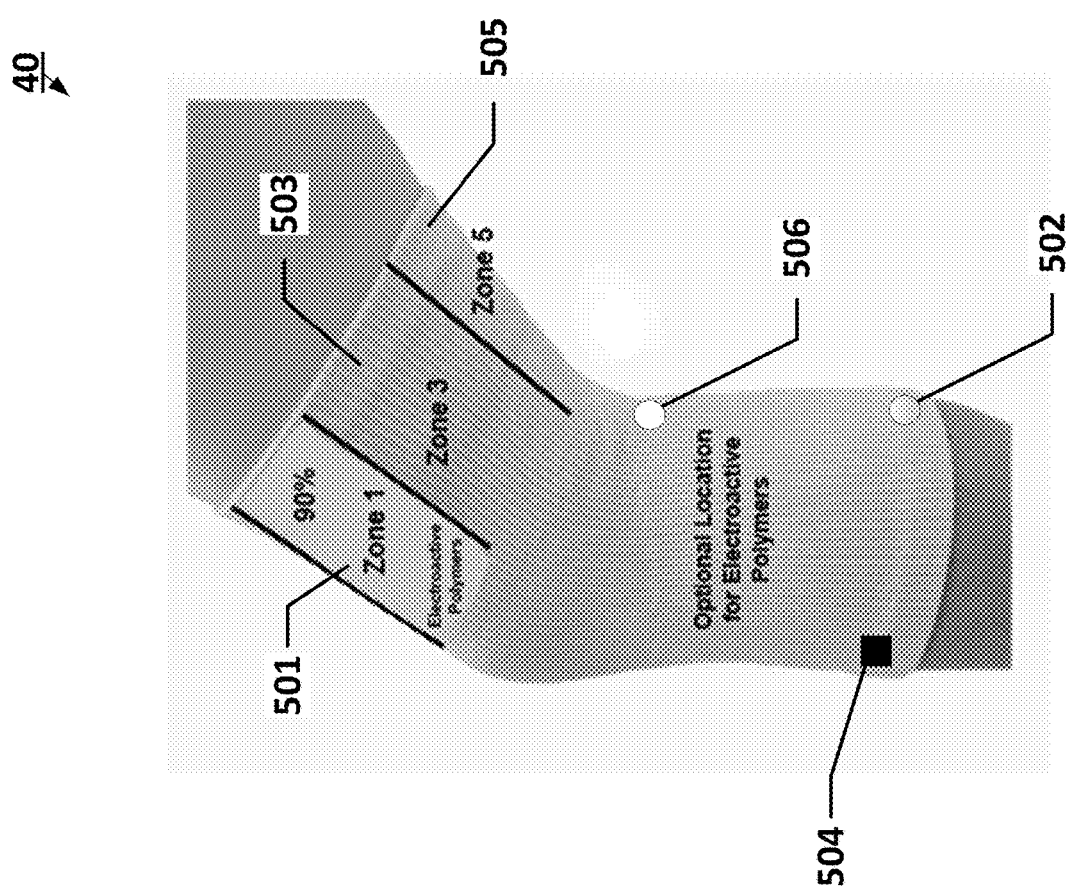
Figure 7B:
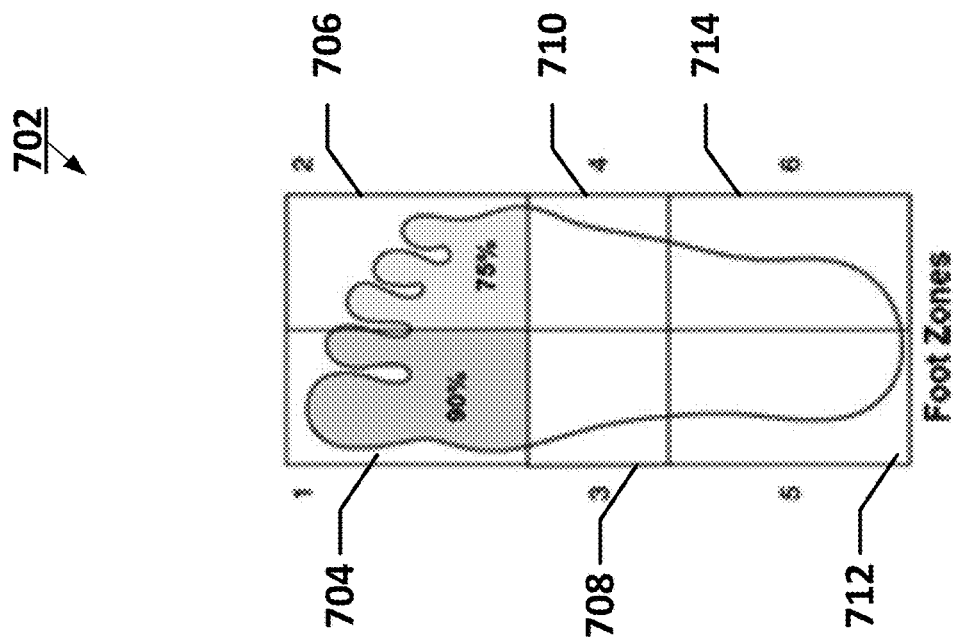
Figure 7A:
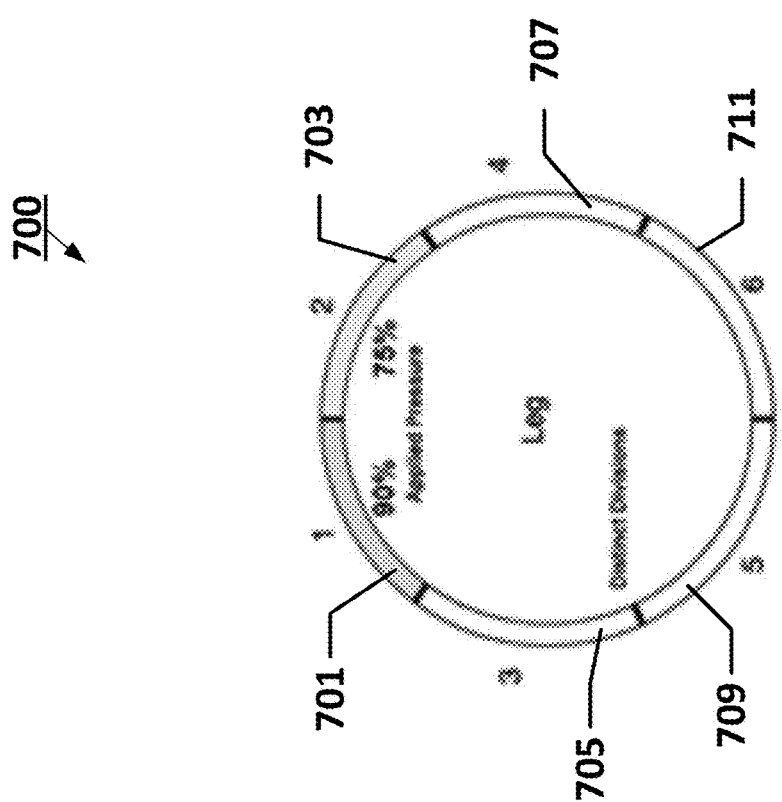
Figure 8:
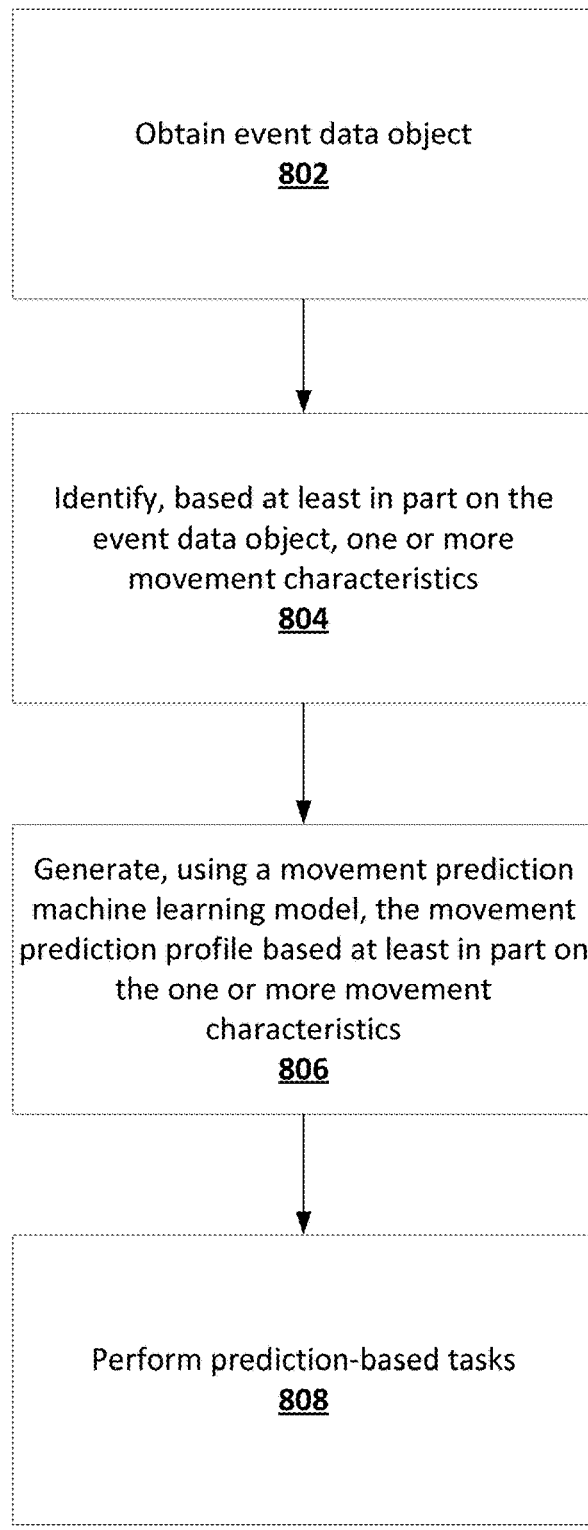
Figure 9:
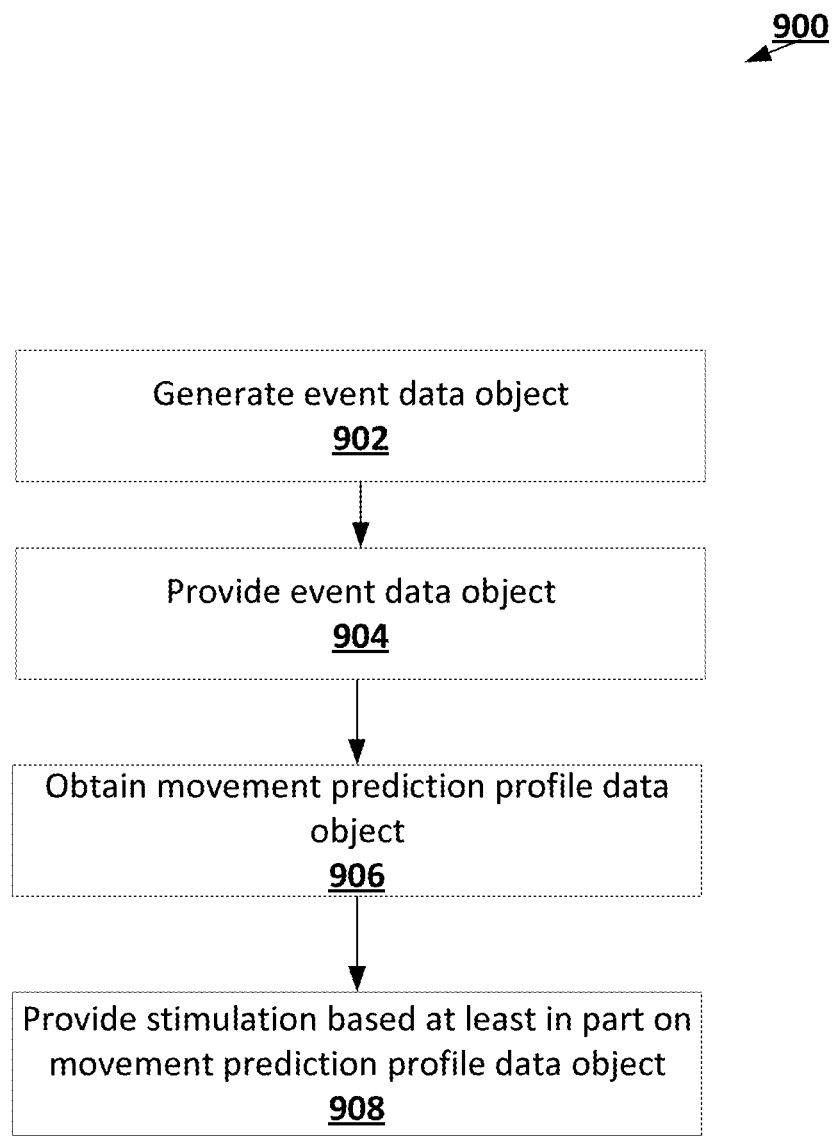
Figure 10:
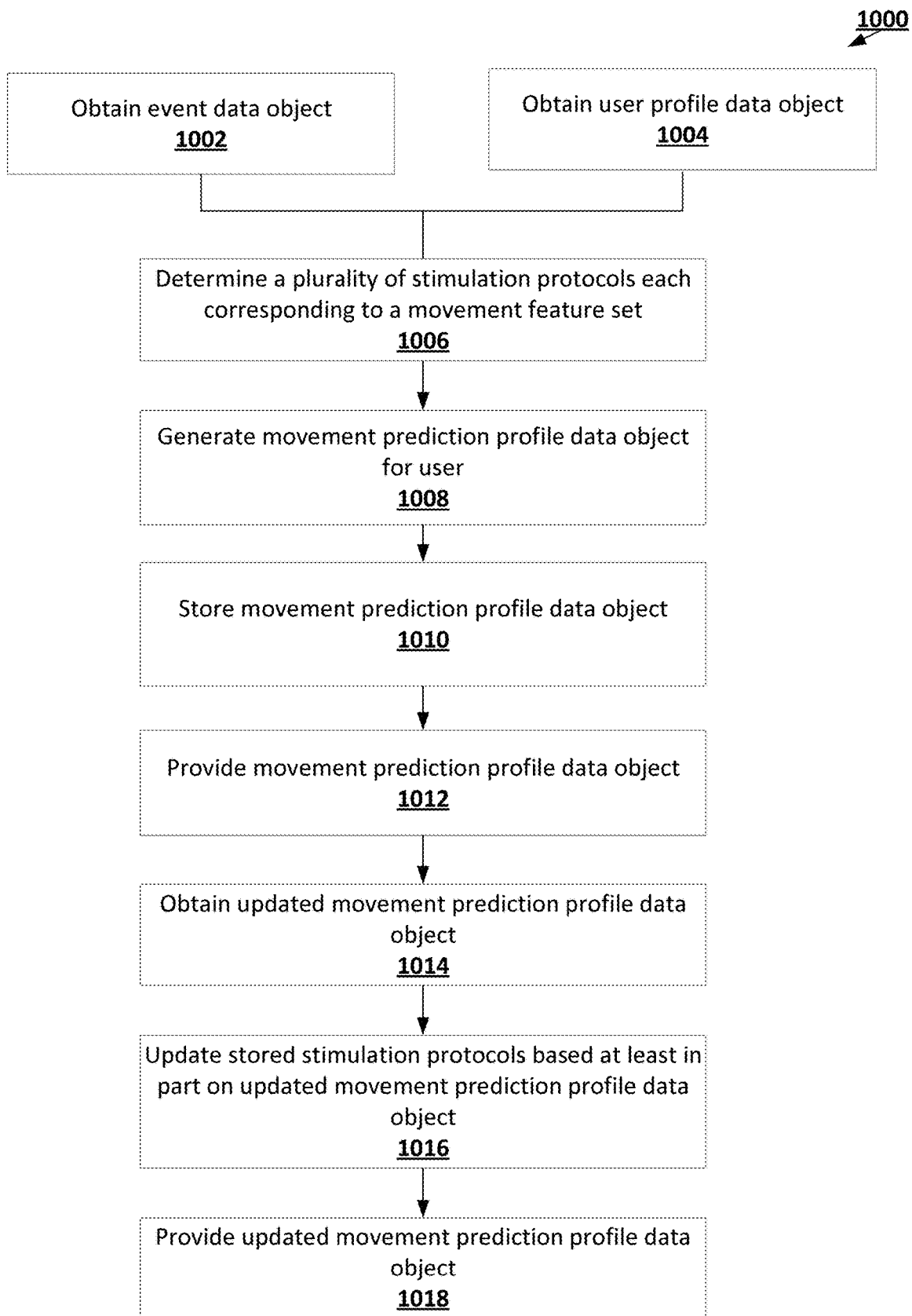
Figure 11:
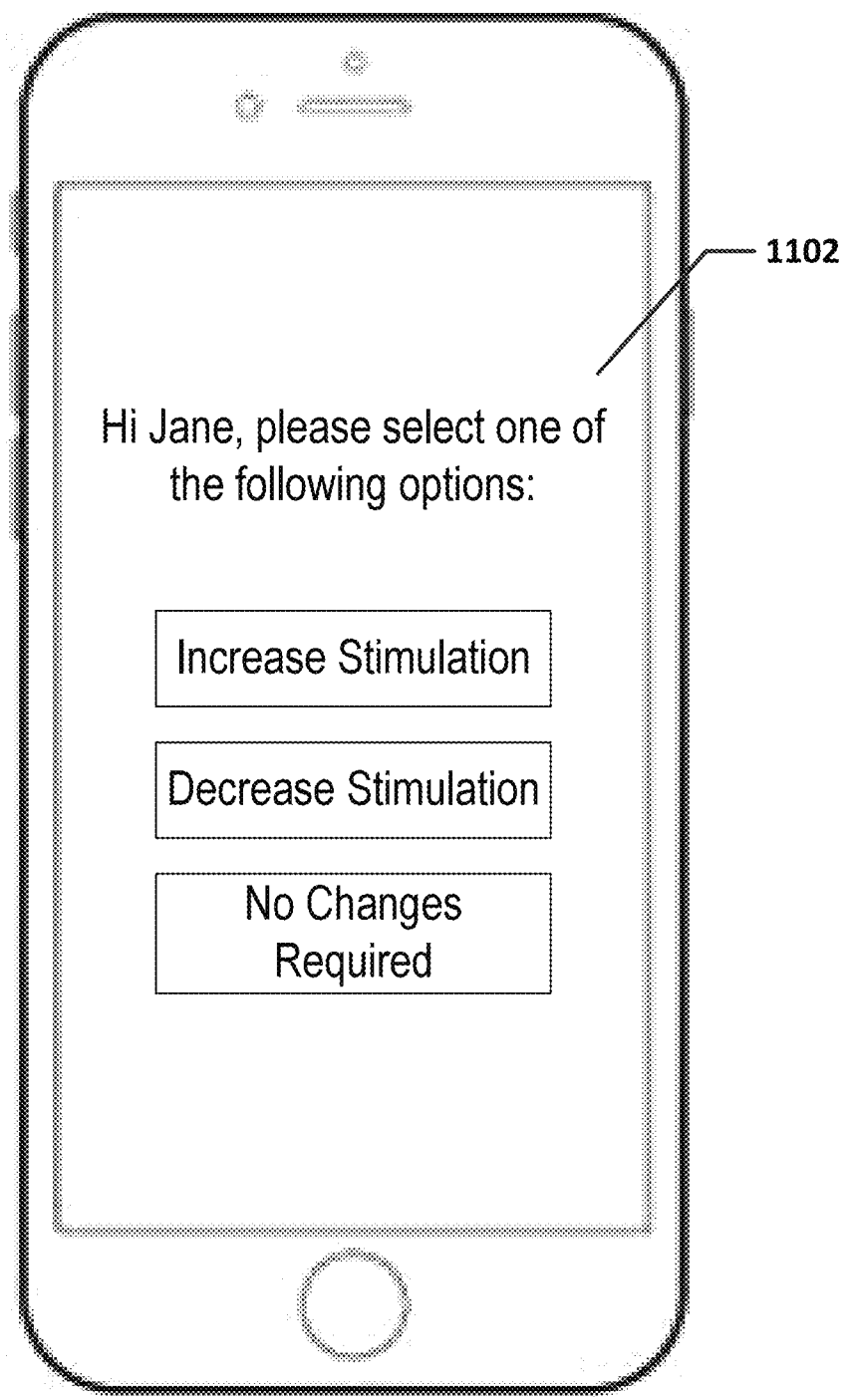

Having thus described the invention in general terms, reference will now be made to the accompanying drawings, which are not necessarily drawn to scale, and wherein:

FIG. 1 is an exemplary overview of a system architecture that can be used to practice various embodiments of the present disclosure;

FIG. 2 is an example schematic of a movement prediction computing entity in accordance with certain embodiments of the present disclosure;

FIG. 3 is an example schematic of a user computing entity in accordance with certain embodiments of the present disclosure;

FIG. 4 is an example schematic of a movement prediction system in accordance with certain embodiments of the present disclosure;

FIG. 5 is an example schematic depicting a wearable device, in accordance with certain embodiments of the present disclosure;

FIG. 6 is an example schematic diagram illustrating sensors in accordance with some embodiments of the present disclosure;

FIG. 7A and FIG. 7B are example schematic diagrams illustrating operational examples in accordance with some embodiments of the present disclosure;

FIG. 8 is a flowchart diagram illustrating an example process in accordance with certain embodiments of the present disclosure;

FIG. 9 is a flowchart diagram illustrating another example process in accordance with certain embodiments of the present disclosure;

FIG. 10 is a flowchart diagram illustrating yet another example process in accordance with certain embodiments of the present disclosure; and FIG. 11 is an example view of a user interface, in accordance with certain embodiments of the present disclosure.

DETAILED DESCRIPTION

Various embodiments of the present disclosure now will be described more fully hereinafter with reference to the accompanying drawings, in which some, but not all embodiments are shown. Indeed, various configurations as discussed herein may be embodied in many different forms and should not be construed as limited to the embodiments set forth herein; rather, these embodiments are provided so that this disclosure will satisfy applicable legal requirements. The term "or" (also designated as "I") is used herein in both the alternative and conjunctive sense, unless otherwise indicated. The terms "illustrative" and "exemplary" are used to be examples with no indication of quality level. Like numbers refer to like elements throughout.

I. Overview and Technical Advantages

Various embodiments of the present invention provide techniques for enabling operations of a wearable device comprising at least one sensor and a plurality of independent sections of electroactive polymers that are each associated with a zone of a wearer's foot, where the wearable device may be configured to: (i) determine motion, orientation and heading with respect to the wearer's foot, (ii) determine characteristics of the wearer's balance, stride and environment, (iii) generate a voltage output via at least one of the plurality of independent sections of electroactive polymers and based at least in part on the determined characteristics, and (iv) dynamically adjust, based at least in part on analysis of historical wearable device data and by utilizing machine learning techniques, the voltage output for each of the plurality of independent sections of electroactive polymers.

Various embodiments are directed to systems, apparatuses, and/or methods for generating a movement prediction profile for use in conjunction with a wearable device that is configured to provide and/or augment stimulation (e.g., nervous system stimulation/feedback).

Various embodiments of the present invention address a need for systems and techniques for generating and providing movement prediction profiles that can account for individual user features and requirements and optimized based at least in part on user input/user response to stimulation over time.

Various embodiments of the present disclosure are directed to a wearable device (e.g., one or two wearable knee braces) having an integrated controller and one or more sensors (e.g., one or more tactile pressure sensors) that are collectively configured to monitor a wearer's movements in real-time and provide stimulation (e.g., via a plurality of independent foot stimulation sections). In some embodiments, stimulation may be provided based at least in part on a movement prediction profile defining a plurality of stimulation protocols. In some embodiments, based at least in part on the movement prediction profile, the controller may provide a control indication to cause one or more of a plurality of independent foot stimulation sections to provide stimulation to one or more target foot zones each associated with a particular area of the foot. A stimulation protocol may be dynamically adjusted based at least in part on user input and/or by monitoring user response. Additionally, the movement prediction profile for a user may be refined over time using machine learning techniques to identify optimal parameters for stimulation protocols. To further enhance system performance, the wearable device may be calibrated based at least in part on user features (e.g., age, gender, biometric information, and/or the like), and any changes thereto. In particular, this system is usable in any stage of peripheral neuropathy and especially during early stages of the condition. As the system is used over time, a wearer's brain will associate stimulation/feedback (e.g., provided in a mid-eg region of the body) with particular angles and positions of the feet while walking. Thus, the system may be used for training and/or neurorehabilitation to assist with regaining mobility and muscle control due to decreased nervous system function.

The apparatuses, systems, and methods described herein provide a robust movement monitoring and stimulation system. Moreover, various embodiments of the present invention disclose movement prediction machine learning models that can make inferences based at least in part on sensor data in a more accurate and computationally efficient manner than state-of-the-art systems. Accordingly, various embodiments of the present disclosure make substantial technical contributions to the field of monitoring devices and substantially improve state-of-the-art systems.

Various embodiments of the present invention improve life experiences of patient affected by peripheral neuropathy (e.g., diabetes patients and stroke victims). Patients affected by peripheral neuropathy (e.g., diabetes patients and stroke victims) may experience reduced mobility as a result of decreased nerve function. For example, a stroke victim may experience degraded nerve connectivity and may need to retrain his or her nervous system to restore nerve function. In some cases, a patient may require an alternate feedback indicator to confirm proper placement of the patient's feet while walking. In the advanced stages of peripheral neuropathy, patients experience a dramatic reduction in their ability to use their feet, which may lead to amputation.

Various embodiments of the present invention address the challenge of increased walking difficulties experienced by patients with peripheral neuropathy. A goal of various embodiments of the present invention is to prevent the progression of peripheral neuropathy using a system that provides simulated nerve feedback to the body relative to foot angle and pressure. In some embodiments, a wearable device is provided that can stimulate the skin (e.g., a mid-leg area of a patient's body) in order to provide linearly synchronized pressure that is controllable by a remote input device. When used over time, the brain is able to associate generated feedback/sensations with the proper angle and position of the feet while walking, enabling patients to recover muscle control. Accordingly, the wearable device may preserve mobility in peripheral neuropathy patients and stall and/or prevent further progression of the condition.

Various embodiments of the present invention disclose a peripheral neuropathy nerve feedback stimulus system. The noted system provides simulated nerve feedback stimulus to the body relative to foot angle and pressure. The system may detect pressure measures in the foot related to walking and standing and correlate these pressure measures to a synchronized feedback system (e.g., in the upper leg), providing a patient with a new source of tactile feedback. The system may thus utilize tactile pressure sensing technologies. In one example, a sole insert consisting of electroactive polymers that trigger an applied voltage in the mid-leg area may provide tactile feedback to the patient. The electroactive polymers may generate a squeezing sensation in a particular zone within the area that is experienced by the patient in direct correlation with the placement of the patient's foot on the ground.

In some embodiments, foot pressure may be detected using tactile pressure sensing technology. The system may be tuned to accommodate different numbers of zones as well as fluctuating pressure levels crossing more than one zone thereby facilitating representation of pressures most analogous to the step pattern of a patient.

The wearable device may be placed in a "learning" mode during calibration in which the wearer standing vertically in a relaxed position (center/balance position) corresponds with 0 volts (no compression) being supplied to the wearable device and therefore no generated feedback. In some examples, calibration operations may be performed under the supervision of a physical therapist or skilled provider. Alternatively, the system can utilize inertial measurement units (IMUs) to determine motion, orientation, and heading with respect to a wearer's feet such as via a sole insert or shoe attachment. The system may convert maximum and minimum angles of the feet to corresponding linear control voltages to be supplied by the wearable device. The system can also work in conjunction with electro-mechanical limbs and provide additional feedback for walking and balance for amputees (e.g., position sensors may be attached directly to a prosthetic). While the patient is walking, the system may detect changes in pressure as the patient's weight is shifted from one foot to another. In some examples, one or more wearable devices can be utilized (e.g., a dual-mode wearable device as described above, with the use of two devices improving system accuracy). In some embodiments, each of a plurality of zones of electroactive polymers may be associated with a particular area of the foot. The wearable device may generate a supply voltage in response to detected pressure in a particular area of the foot. The resulting sensation in the wearer's leg will be distinctive depending on the zone to which voltage is supplied, allowing the wearer to detect/feel the position of his or her foot. In some embodiments, a center/balanced position may correspond with 0 volts (i.e., no compression of the wearable device material).

Analysis of pressure levels in each wearable device zone can facilitate selection of a control voltage output to each of the corresponding zones of the leg area through the wearable device. Various wireless technologies may be utilized to transmit data between the wearable device and another computing device. Alternative embodiments may include techniques that stimulate sensory nerves near the epidermis. For example, by deploying mechanical forces via small actuators (e.g., heat or vibrating elements) that can be interpreted by sensory nerves. The control voltage may be varied in order to increase or decrease the intensity of the pressure (compression) of the wearable device. Machine learning techniques may also be used to analyze the wearer's balance, stride and environment, e.g., to automatically adjust the voltage level being supplied by the wearable device. In some embodiments, machine learning techniques may be utilized to generate user guidance and/or provide alerts to the wearer (e.g., regarding over-exertions, difficult terrains, or unsuccessful operations).

II. Definitions of Certain Terms

The term "body" may refer to a person's physical form, and the term may specifically be utilized to refer to a portion of a person's body, including at least a portion of one or more internal and/or external organs of a user. In general, the terms user, patient, wearer, individual, person and/or similar words are used herein interchangeably.

The term "electronically coupled" or "in electronic communication with" may refer to two or more electrical elements (for example, but not limited to, an example processing circuitry, communication module, input/output module memory, plurality of independent foot stimulation sections) and/or electric circuit(s) being connected through wired means (for example but not limited to, conductive wires or traces) and/or wireless means (for example but not limited to, wireless network, electromagnetic field), such that data and/or information (for example, electronic indications, signals) may be transmitted to and/or received from the electrical elements and/or electric circuit(s) that are electronically coupled.

The term "peripheral neuropathy" may refer to a condition in which damage to the peripheral nervous system associated with the brain and spinal cord causes weakness, numbness and/or pain, particularly in the hands and feet. Peripheral neuropathy can be caused by injury, infections, metabolic disease (e.g., diabetes), exposure to toxins, or the like. Patients affected by peripheral neuropathy in the feet, particularly diabetes induced peripheral neuropathy, may experience reduced mobility as a result of decreased nerve function. In another example, a stroke victim may experience degraded nerve connectivity and may need to retrain his or her nervous system in order to restore nerve function. In some examples, a lack of stimulation/feedback from the nervous system results in walking difficulties as peripheral neuropathy progresses and can lead to amputation.

The term "wearable device" may refer to an article or garment configured to fit closely to a wearer's body. In some embodiments, the wearable device may be or comprise an electronic device that is configured to be worn proximate or adjacent a wearer's knee, leg or thigh (e.g., one or two wearable knee braces). In some embodiments, the wearable device may be or comprise, for example without limitation, a jacket, vest, shirt, pants, shorts, underwear, hat, socks, scarf, neck warmer, leg gaiter, head band, arm band, leg band, and/or the like. In some embodiments, the wearable device comprises a plurality of independent stimulation sections that are each associated with a particular foot zone of the wearer. In various embodiments, an example wearable device may comprise at least a power source (e.g., a rechargeable battery), a controller or processor, a wireless communication transceiver and one or more sensors.

The term "sensor data" may refer to one or more data objects describing user balance information/data, physiological information/data, biometric information/data, accelerometer information/data, location information/data, environmental information/data, image/video sensor information/data, and/or the like which may be associated with a particular person (e.g., a user of a wearable device). Sensor data may be collected and/or generated by one or more sensors associated with the user, such as mobile device sensors, wearable device sensors (e.g., one or more tactile pressure sensors), sensors associated with one or more devices commonly used by the user, and/or the like. In some embodiments, embodiments, the sensor data may include image data, muscle condition data, heart rate data, oxygen saturation data, pulse rate data, body temperature data, breath rate data, perspiration data, blink rate data, blood pressure data, neural activity data, cardiovascular data, pulmonary data, and/or various other types of information/data. In some embodiments, sensor data may be stored in conjunction with a user profile.

The term "movement prediction machine learning model" may refer to a data object that describes steps/operations, hyper-parameters, and/or parameters of a machine learning model/algorithm that is configured to generate data needed to infer/generate a movement profile with respect to a person (e.g., a user of a wearable device). The steps/operations of the movement prediction machine learning model may lead to performing one or more prediction-based tasks (e.g., providing the movement prediction profile for use in conjunction with a wearable device in order to provide stimulation while a user is walking). In some embodiments, the movement prediction machine learning model may comprise a first sub-model that is configured to generate a movement prediction profile comprising one or more movement feature sets. In some embodiments, the movement prediction machine learning model may comprise a second sub-model that is configured to generate a plurality of stimulation protocols that are each associated with a particular movement feature set. By way of example, a movement feature set may comprise user balance information and environmental information. In some embodiments, a movement feature set may be or comprise a gradient representation of pressure distribution across at least a portion of a user's foot. The movement prediction machine learning model may be trained based at least in part on a ground truth event data object. By way of example, the movement prediction machine learning model/algorithm may be a neural network, a convolutional neural network (CNN), a recurrent neural network (RNN), and/or the like.

The term "movement prediction profile" may refer to a data object that describes a predictive output of one or more computer-implemented processes, wherein the predictive output describes a plurality of movement feature sets associated with a particular user in which each movement feature set comprises a gradient representation of pressure distribution across at least a portion of a user's foot. In some embodiments, each movement feature set is associated with a particular foot movement, foot position, foot angle and/or pressure distribution. By way of example, a first movement feature set may be associated with a user's standing position when both feet are in contact with the ground. Another movement feature set may be associated with a user's walking stride. In an example walking stride, a user's right foot may be up in the air (i.e., not in contact with the ground) and at least a portion of the user's left foot may be in contact with the ground. In another example walking stride, at least a portion of a user's right foot may be in contact with the ground and the entirety of the user's left foot may be in the air. In some embodiments, determining a movement prediction profile may comprise processing an event data object describing sensor data associated with a user of a wearable device. In some embodiments, the movement prediction profile may be an output of movement prediction machine learning model. Additionally, in some embodiments, determining the movement prediction profile may comprise identifying a stimulation protocol for each movement feature set.

The term "event data object" may refer to a data object storing and/or providing access to information/data that is related a user of a wearable device (e.g., describes recorded movements of the noted user). In some embodiments, an event data object may describe one or more recorded events associated with a user of a wearable device. In some embodiments, the event data object may comprise sensor data (e.g., foot pressure distribution information/data, image information/data, location information/data, and/or the like) associated with a user's foot/feet, the user's movements, the user's environment, combinations thereof, and/or the like. In some embodiments, an event data object may comprise audio information/data, image/video sensor information/data, physiological information/data, biometric information/data, accelerometer information/data, environmental information/data, combinations thereof, and/or the like.

The term "stimulation protocol" may refer to a data object that describes one or more electrical pulses (e.g., a sequence of electrical pulses) that are associated with a target foot zone and/or at least one of a plurality of independent stimulation sections of a wearable device. Each electrical pulse may be defined by one or more characteristics (i.e., electrical pulse characteristics) including, without limitation, intensity (e.g., defined by amplitude, voltage and/or current characteristics), duration (e.g., pulse duration), wave type and/or wave form. In some embodiments, a stimulation protocol may be associated with a movement feature set. A stimulation protocol may be triggered/initiated in response to detecting one or more movement characteristics associated with a user of a wearable device that are associated with a movement feature set. In various embodiments, a stimulation protocol may be delivered to at least one target foot zone via one or more independent stimulation sections positioned adjacent the at least one target foot zone. By way of example, a stimulation protocol for a standing position in which a user has both feet placed firmly on the ground may comprise providing no stimulation. In another example, a stimulation protocol for a walking stride in which a front portion of a user's right foot is in contact with the ground while a back portion of the right foot is in the air may comprise providing stimulation to one or more target foot zones associated with the front portion of the right foot. Additionally, if the entirety of the user's left foot is in contact with the ground, the stimulation protocol may also comprise providing no stimulation to the user's left foot. Accordingly, while a user is walking within a particular environment/terrain, a wearable device may provide stimulation (e.g., electrical pulses) to one or more target foot zones based at least in part on a current location/position of the user's foot relative to the ground.

III. Computer Program Products, Methods, and Computing Devices

Embodiments of the present disclosure may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In some embodiments, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In some embodiments, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 provides an example system architecture 100 that can be used in conjunction with various embodiments of the present disclosure. As shown in FIG. 1, the system architecture 100 may comprise one or more movement prediction computing entities 10, one or more user computing entities 20, one or more networks 30, one or more wearable devices 40 and/or the like. Each of the components of the system may be in electronic communication with, for example, one another over the same or different wireless or wired networks 30 including, for example, a wired or wireless Personal Area Network (PAN), Local Area Network (LAN), Metropolitan Area Network (MAN), Wide Area Network (WAN), and/or the like. Additionally, while FIG. 1 illustrates certain system devices as separate, standalone devices, the various embodiments are not limited to this particular architecture.

Exemplary Movement Prediction Computing Entity

FIG. 2 provides a schematic of a movement prediction computing entity 10 according to some embodiments of the present disclosure. In general, the terms computing device, entity, device, system, and/or similar words used herein interchangeably may refer to, for example, one or more computers, computing devices, computing entities, desktop computers, mobile phones, tablets, phablets, notebooks, laptops, distributed systems, terminals, servers or server networks, blades, gateways, switches, processing devices, set-top boxes, relays, routers, network access points, base stations, the like, and/or any combination of devices adapted to perform the functions, operations, and/or processes described herein. Such functions, operations, and/or processes may include, for example, transmitting, receiving, operating on, processing, displaying, storing, determining, generating/creating, monitoring, evaluating, comparing, and/or similar terms used herein interchangeably. In some embodiments, these functions, operations, and/or processes can be performed on data, content, information, and/or similar terms used herein interchangeably.

As indicated, in some embodiments, the movement prediction computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like.

As shown in FIG. 2, In some embodiments, the movement prediction computing entity 10 may include or be in communication with one or more processing elements 205 (also referred to as processors, processing circuitry, and/or similar terms used herein interchangeably) that communicate with other elements within the movement prediction computing entity 10 via a bus, for example. As will be understood, the processing element 205 may be embodied in a number of different ways. For example, the processing element 205 may be embodied as one or more complex programmable logic devices (CPLDs), microprocessors, multi-core processors, coprocessing devices, application-specific instruction-set processors (ASIPs), and/or controllers. Further, the processing element 205 may be embodied as one or more other processing devices or circuitry. The term circuitry may refer to an entire hardware embodiment or a combination of hardware and computer program products. Thus, the processing element 205 may be embodied as integrated circuits, application specific integrated circuits (ASICs), field-programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In some embodiments, the movement prediction computing entity 10 may further include or be in communication with non-volatile media (also referred to as non-volatile storage, memory, memory storage, memory circuitry and/or similar terms used herein interchangeably). In some embodiments, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In some embodiments, the movement prediction computing entity 10 may further include or be in communication with volatile media (also referred to as volatile storage, memory, memory storage, memory circuitry and/or similar terms used herein interchangeably). In some embodiments, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the movement prediction computing entity 10 with the assistance of the processing element 205 and the operating system.

As indicated, in some embodiments, the movement prediction computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, movement prediction computing entity 10 may be configured to communicate via wireless external communication networks using any of a variety of protocols, such as general packet radio service (GPRS), Universal Mobile Telecommunications System (UMTS), Code Division Multiple Access 200 (CDMA200), CDMA200 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), IR protocols, NFC protocols, RFID protocols, IR protocols, ZigBee protocols, Z-Wave protocols, 6LoWPAN protocols, Wibree, Bluetooth protocols, wireless universal serial bus (USB) protocols, and/or any other wireless protocol. The movement prediction computing entity 10 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the movement prediction computing entity's components may be located remotely from other movement prediction computing entity 10 components, such as in a distributed system. Furthermore, one or more of the components may be aggregated and additional components performing functions described herein may be included in the movement prediction computing entity 10. Thus, the movement prediction computing entity 10 can be adapted to accommodate a variety of needs and circumstances, such as including various components described with regard to a mobile application executing on the user computing entity 20, including various input/output interfaces.

Exemplary User Computing Entity

The user computing entity 20 may be in communication with the movement prediction computing entity 10 and the wearable device 40. The user computing entity 20 may obtain and provide (e.g., transmit/send) data objects describing raw data (e.g., sensor data and/or physiological data associated with the user) obtained by one or more additional sensors or sensing devices, captured by another user computing entity 20 or device and/or provided by another computing entity. The user computing entity 20 may be configured to provide (e.g., transmit, send) data objects describing at least a portion of the sensor data and/or physiological data to the movement prediction computing entity 10. Additionally, in various embodiments, a remote computing entity may provide data objects describing user information/data to the movement prediction computing entity 10. In some embodiments, a user (e.g., wearer) of the wearable device 40 may operate the wearable device 40 via the display 316 or keypad 318 of the user computing entity 20.

FIG. 3 provides an illustrative schematic representative of user computing entity 20 that can be used in conjunction with embodiments of the present disclosure. In various embodiments, the user computing entity 20 may be or comprise one or more mobile devices. For example, a user computing entity 20 may be embodied as a user's mobile device, carried by the user, and therefore the user computing entity 20 may be in close proximity to a wearable device worn by the user, such that close-range wireless communication technologies may be utilized for communicating between a controller of a wearable device and the user computing entity 20.

As shown in FIG. 3, a user computing entity 20 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various devices, such as a movement prediction computing entity 10, another user computing entity 20, and/or the like. In an example embodiment, the transmitter 304 and/or receiver 306 are configured to communicate via one or more SRC protocols. For example, the transmitter 304 and/or receiver 306 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 312, transmitter 304, and receiver 306 may be configured to communicate via one or more long range protocols, such as GPRS, UMTS, CDMA200, 1×RTT, WCDMA, GSM, EDGE, TD-SCDMA, LTE, E-UTRAN, EVDO, HSPA, HSDPA, Wi-Fi, Wi-Fi Direct, WiMAX, and/or the like. The user computing entity 20 may also include one or more network and/or communications interfaces 320 for communicating with various computing entities, such as by communicating data, content, information, and/or similar terms used herein interchangeably that can be transmitted, received, operated on, processed, displayed, stored, and/or the like.

In this regard, the user computing entity 20 may be capable of operating with one or more air interface standards, communication protocols, modulation types, and access types. More particularly, the user computing entity 20 may operate in accordance with any number of wireless communication standards and protocols. In a particular embodiment, the user computing entity 20 may operate in accordance with multiple wireless communication standards and protocols, such as GPRS, UMTS, CDMA200, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 20 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 20 can also download changes, add-ons, and updates, for instance, to its firmware, software (e.g., including executable instructions, applications, program modules), and operating system.

According to some embodiments, the user computing entity 20 may include location determining aspects, devices, modules, functionalities, and/or similar words used herein interchangeably to acquire location information/data regularly, continuously, or in response to certain triggers. For example, the user computing entity 20 may include outdoor positioning aspects, such as a location module adapted to acquire, for example, latitude, longitude, altitude, geocode, course, direction, heading, speed, UTC, date, and/or various other information/data. In some embodiments, the location module can acquire information/data, sometimes known as ephemeris information/data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the apparatus's 30 position in connection with a variety of other systems, including cellular towers, Wi-Fi access points, and/or the like. Similarly, the user computing entity 20 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The user computing entity 20 may also comprise a user interface device comprising one or more user input/output interfaces (e.g., a display 316 and/or speaker/speaker driver coupled to a processing element 308 and a touch interface, keyboard, mouse, and/or microphone coupled to a processing element 308). For example, the user interface may be configured to provide a mobile application, browser, interactive user interface, dashboard, webpage, and/or similar words used herein interchangeably executing on and/or accessible via the user computing entity 20 to cause the display or audible presentation of information/data and for user interaction therewith via one or more user input interfaces. Moreover, the user interface can comprise or be in communication with any of a number of devices allowing the user computing entity 20 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 20 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 20 can capture, collect, store information/data, user interaction/input, and/or the like.

The user computing entity 20 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, information/data, applications, programs, program modules, scripts, source code, object code, byte code, compiled code, interpreted code, machine code, executable instructions, and/or the like to implement the functions of the user computing entity 20.

Exemplary Movement Prediction System

FIG. 4 is a schematic diagram of an example system architecture 400 for generating movement prediction profiles that can be used to perform one or more prediction-based tasks. The architecture 400 includes a movement prediction system 401 that is configured to receive data from the client computing entities 402, process the data to generate predictive outputs (e.g., movement prediction profile data objects), and provide the outputs to the client computing entities 402 (e.g., for generating user interface data and/or dynamically updating a user interface). In some embodiments, movement prediction system 401 may communicate with at least one of the client computing entities 402 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The movement prediction system 401 may include a movement prediction computing entity 406 and a storage subsystem 408. The movement prediction computing entity 406 may be configured to receive queries, requests and/or data from client computing entities 402, process the queries, requests and/or data to generate predictive outputs, and provide (e.g., transmit, send, and/or the like) the predictive outputs to the client computing entities 402. The client computing entities 402 may be configured to transmit requests to the movement prediction computing entity 406 in response to queries. Responsive to receiving the predictive outputs, the client computing entities 402 may generate user interface data and may provide (e.g., transmit, send and/or the like) user interface data for presentation by user computing entities.

The storage subsystem 408 may be configured to store at least a portion of the data utilized by the movement prediction computing entity 406 to perform movement prediction operations and tasks. The storage subsystem 408 may be configured to store at least a portion of operational data and/or operational configuration data including operational instructions and parameters utilized by the movement prediction computing entity 406 to perform movement prediction operations/tasks in response to requests. The storage subsystem 408 may include one or more storage units, such as multiple distributed storage units that are connected through a computer network. Each storage unit in the storage subsystem 408 may store at least one of one or more data assets and/or one or more data about the computed properties of one or more data assets. Moreover, each storage unit in the storage subsystem 408 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Wearable Device

FIG. 5 is a schematic diagram illustrating an example wearable device 40 in accordance with some embodiments of the present disclosure. In various embodiments, the wearable device 40 is configured to provide stimulation/feedback associated with one or more target foot zones of a wearer's foot/feet (e.g., via a plurality of independent foot stimulation sections).

As noted above, the wearable device 40 may be or comprise an article configured to be worn proximate or adjacent a wearer's knee, leg and/or thigh. As depicted in FIG. 5, the wearable device 40 comprises a wearable knee brace configured to be worn over or adjacent the wearer's knee, including at least a portion of the lower thigh and upper calf. In some embodiments, the wearable device 40 comprises a stretchable fabric or other materials (e.g., cotton, foam, polyester, spandex, molded elastic, combinations thereof, or the like). In some embodiments, as depicted in FIG. 5, the example wearable device 40 comprises at least a first independent foot stimulation section 501, a second independent foot stimulation section 503, a third independent foot stimulation section 505, a controller 502 (e.g., processor and/or a wireless communication transceiver), a power source 504 (e.g., a rechargeable battery) and at least one inertial measurement unit (IMU) 506. In some embodiments, the wearable device 40 comprises a single wearable knee brace. In some embodiments, the wearable device 40 comprises a first wearable knee brace configured to be worn over/adjacent a first knee and a second wearable knee brace configured to be worn over/adjacent a second knee. In such embodiments, the first wearable knee brace and the second wearable knee brace may be operatively coupled to one another and in electronic communication with one another.

While FIG. 5 provides an example wearable device 40, it is noted that the scope of the present disclosure is not limited to the example shown in FIG. 5. In some embodiments, the wearable device 40 may comprise one or more additional and/or alternative elements, and/or may be different from that illustrated in FIG. 5. In some embodiments, the wearable device 40 may be or comprise a jacket, vest, shirt, pants, shorts, underwear, hat, socks, scarf, neck warmer, leg gaiter, head band, arm band, leg band, and/or the like. It should be understood that the wearable device 40 can be configured to we worn adjacent any part of the body where placement consistency can be exercised and may be used in conjunction with a variety of mobility assistive devices including wheelchairs, prosthetics, foot-controlled devices, or the like. Additionally and/or alternatively, the wearable device 40 may be configured to provide stimulation with respect to a wearer's hands or fingers. In some embodiments, the wearable device 40 may comprise or be in electronic communication with one or more additional sensors such as tactile pressure sensors, IMUs, image sensors, accelerometers, gyroscopes, combinations thereof, and/or the like.

As further depicted in FIG. 5, the example wearable device 40 comprises at least one IMU 506 attached to a surface of the wearable device 40. The at least one IMU 506 may be attached to any interior or exterior surface of the wearable device 40 and in some examples may be integrated within the wearable device 40. The at least one IMU 506 may detect and report measurements associated with a body's specific force, angular rate, orientation, acceleration, angular velocity, and/or the like. The at least one example IMU 506 may include one or more accelerometers, gyroscopes and magnetometers. In some embodiments, the at least one IMU 506 and/or other sensors may be configured to detect and record measurements relating to user balance information and/or environmental information (e.g., relating to a type of terrain that the user is walking on, user activity or the like). In some embodiments (e.g., in which the wearable device 40 comprises two wearable knee braces), the wearable device may comprise one or more line-of-sight sensors configured to detect unintended rotations of the wearable device 40 by measuring changes in the distance between the line-of-sight sensors or detecting an absence of a line-of-sight reading. In some embodiments, the wearable device 40 may comprise Hall-effect or variable reluctance (VR) sensors that operate to measure rotational positions with respect to one another and facilitate proper positioning of the wearable device 40. In some embodiments, visual or audible indicators (e.g., provided via the user computing entity 20) may be provided to alert a wearer in an instance in which an unintended rotation or incorrect placement of one or both wearable knee braces occurs. In some embodiments, the wearable device 40 may comprise additional sensors (e.g., attached to an interior surface of the wearable device 40) that are configured to obtain data/information with respect to adjacent regions of the wearer's body (e.g., temperature, moisture level, heartrate information or the like) that can be used to facilitate proper positioning of the wearable device 40.

Referring now to FIG. 6, a schematic diagram 600 illustrating example sensors configured to be in electronic communication with a wearable device 40 in accordance with some embodiments of the present disclosure is provided.

As depicted in FIG. 6, the wearable device 40 is in electronic communication with/operatively coupled to a first tactile pressure sensor 601 and a second tactile pressure sensor 603. In various embodiments, the first tactile pressure sensor 601, the second tactile pressure sensor 603 and/or other sensors may be positioned at least partially on any interior or exterior surface of footwear worn by a wearer of the wearable device. In some embodiments, at least one sensor (e.g., the first tactile pressure sensor 601 and/or IMU) may be attached or positioned directly onto a portion of the wearer's body, leg or prosthetic. As illustrated, each of the first tactile pressure sensor 601 and the second tactile pressure sensor 603 comprises an insole or shoe insert configured to be at least partially disposed within footwear. In particular, the first tactile pressure sensor 601 may be positioned adjacent an inner surface of a first shoe and a second tactile pressure sensor 603 may be positioned adjacent an inner surface of a second shoe. At least one sensor of the wearable device 40 (e.g., the first tactile pressure sensor 601, the second tactile pressure sensor 603, IMU(s) and/or other sensors) may be configured to capture sensor data comprising real-time user movement data. For example, the at least one sensor may be configured to capture user balance data/information (e.g., orientation data, heading data, foot movement, foot position, foot angle and/or pressure distribution), environmental data/information (e.g., terrain information), combinations thereof, and/or the like. In certain embodiments, the at least one sensor enables receiving and/or capturing raw sensor information/data (e.g., regularly, continuously, and/or in response to certain triggers). In some embodiments, as discussed herein, each tactile pressure sensor 601, 603 may associate detected patterns with a configurable number of foot zones. Accordingly, an operator (e.g., clinician) may select a number and/or distribution of foot zones that is most analogous to a wearer's step patterns.

In some embodiments, the wearable device 40 may comprise microelectromechanical (MEMS) components, biological and chemical sensing components, electrocardiogram (ECG) components, electromyogram (EMG) components, electroencephalogram (EEG)-based neural sensing components, optical sensing components, electrical sensing components, sound components, vibration sensing components, accelerometer(s), pressure sensor(s) and/or the like. In certain embodiments, the at least one sensor may comprise a plurality of sensors of various sensor types to capture multiple data types. In certain embodiments, sensor data from one or more sensors (e.g., the first tactile pressure sensor 601 and/or the second tactile pressure sensor 603) may be analyzed (e.g., locally by the controller 502 of the wearable device 40 or via the movement prediction computing entity 10) to generate a movement prediction profile. Through such components, various types of physiological information/data can be captured—such as body position and/or movement data/information, heart rate information/data, oxygen saturation information/data, body temperature information/data, breath rate information/data, perspiration information/data, neural information/data, cardiovascular sounds information/data, and/or various other types of information/data. The one or more sensors of the wearable device 40 may be in electronic communication with the controller 502 of the wearable device 40 such that they can exchange information/data (e.g., receive and transmit data) with the wearable device 40. Additionally, sensor data may be collected and/or generated by one or more sensors associated with the user, such as mobile device sensors, other wearable device sensors (e.g., a smartwatch), sensors associated with one or more devices commonly used by the user (e.g., a glucose monitoring device), and/or the like.

In some embodiments, the controller 502 of the wearable device 40 (e.g., which may comprise a computing device, one or more computer processors, or the like) may include a wireless communication transceiver and/or the like. In various embodiments, the controller 502 of the wearable device 40 may comprise components similar or identical to the user computing entity 20 depicted in FIG. 3. The controller 502 may be integrated into or attached to any surface of the wearable device 40 and may be in wired or wireless communication with various elements (e.g., the first independent foot stimulation section 501, the second independent foot stimulation section 503, the third independent foot stimulation section 505, one or more tactile pressure sensors, additional sensors described above and/or the like) of the wearable device 40, and the power source 504 of the wearable device. Accordingly, the controller 502 of the wearable device 40 may be configured to (e.g., alone or together with the movement prediction computing entity 10) provide appropriate signals to elements of the wearable device 40 in order to provide stimulation/feedback (e.g., via one or more of a plurality of independent foot stimulation sections). In some embodiments, the controller 502 may be in wireless communication with, but be physically distinct from, the wearable device 40 (e.g., via short-range wireless communication, such as Bluetooth communication, via long-range wireless communication, and/or the like), which may encompass a wireless receiver, thereby enabling appropriate signals to be passed to the wearable device 40 as discussed herein. In certain embodiments, the controller 502 may comprise an input/output interface system comprising one or more user input/output interfaces (e.g., a button, a display, and a touch interface, and/or a microphone coupled to a processing element and/or controller). For example, the user interface may be configured to cause display of or present audible presentation of information/data and for user interaction therewith via one or more user input interfaces. The controller 502 may store instructions/parameters required for various operations by the wearable device 40.

As noted above, the wearable device 40 comprises a plurality of independent foot stimulation sections. In particular, as depicted in FIG. 5, the wearable device 40 comprises at least a first independent foot stimulation section 501, a second independent foot stimulation section 503 and a third independent foot stimulation section 505. Each of the plurality of independent foot stimulation sections 501, 503, 505 of the wearable device 40 may comprise electroactive polymers that exhibit a change in shape or size (e.g., contract, deform, or the like) in response to an applied electric field (e.g., an electrical current or voltage) and may each comprise an electrode or other electrical device that is configured to independently receive and/or transmit electrical signals. The electroactive polymers may revert to their original state/shape when the electric field is no longer present. Additionally and/or alternatively, a wearable device 40 may provide stimulation via mechanical actuators, heating elements, vibrational devices, and/or the like.

In various embodiments, each of the plurality of independent foot stimulation sections is associated with a particular foot zone of the wearer and may be configured to be positioned adjacent the foot zone. For example, as depicted, the first independent foot stimulation section 501 is associated with a top left area of a wearer's foot, the second independent foot stimulation section 503 is associated with a central left area of the wearer's foot and the third independent foot stimulation section 505 is associated with a bottom left area of the wearer's foot.

Referring now to FIG. 7A and FIG. 7B, schematic diagrams illustrating operational examples 700 and 702 of a plurality of independent foot stimulation sections of a wearable device 40 in accordance with some embodiments of the present disclosure are provided.

In particular, as depicted in FIG. 7A, the wearable device 40 comprises a first independent foot stimulation section 701, a second independent foot stimulation section 703, a third independent foot stimulation section 705, a fourth independent foot stimulation section 707, a fifth independent foot stimulation section 709 and a sixth independent foot stimulation section 711. Each of the plurality of independent foot stimulation section's 701, 703, 705, 707, 709 and 711 is configured to be positioned adjacent a particular portion/zone of a wearer's leg/knee.

In some embodiments, each of the plurality of independent foot stimulation section's may provide stimulation (e.g., deform, contract) to a corresponding foot zone in response to detected user balance information (e.g., pressure, foot angle, foot position, combinations thereof, and/or the like) associated with the particular foot zone that satisfies one or more parameters. As illustrated in FIG. 7B, each of the first independent foot stimulation section 701, the second independent foot stimulation section 703, the third independent foot stimulation section 705, the fourth independent foot stimulation section 707, the fifth independent foot stimulation section 709 and the sixth independent foot stimulation section 711 is associated with a particular foot zone of a wearer. For example, as depicted, the first independent foot stimulation section 701 is associated with a first zone 704 corresponding with a top left area of the wearer's foot. As further depicted, the second independent foot stimulation section 703 is associated with a second foot zone 706 corresponding with a top right area of the wearer's foot. The third independent foot stimulation section 705 is associated with a third foot zone 708 corresponding with a central left area of the wearer's foot. The fourth independent foot stimulation section 707 is associated with a fourth foot zone 710 corresponding with a central right area of the wearer's foot. The fifth independent foot stimulation section 709 is associated with a fifth foot zone 712 corresponding with a bottom left area of the wearer's foot. The sixth independent foot stimulation section 711 is associated with a sixth foot zone 714 corresponding with a bottom right area of the wearer's foot.

In some embodiments, the wearable device 40 may store and utilize a movement prediction profile for a wearer. As noted above, the movement prediction profile may be a data object that describes a plurality of movement feature sets associated with a particular user. In some embodiments, each movement feature set comprises a gradient representation of pressure distribution across at least a portion of a user's foot. Additionally, each movement feature set may be associated with a particular foot movement, foot position, foot angle, foot pressure distribution and stimulation protocol. For example, a first movement feature set may be associated with a user's standing position when both feet are placed firmly on the ground. Another movement feature set may be associated with a user's particular walking stride. In an example walking stride, a user's right foot may be partially in contact with the ground while the user's left foot may be up in the air. In various embodiments, the wearable device 40 may provide a control indication to cause a particular independent foot stimulation section to provide stimulation based at least in part on a stored stimulation protocol. By way of example, in an instance in which a front portion of a wearer right foot (e.g., corresponding with the first foot zone 704 and the second foot zone 706) is in contact with the ground while the wearer is walking, 90% applied pressure may be detected in the first foot zone 704 and 70% applied pressure may be detected in the second foot zone 706 (e.g., via a tactile pressure sensor). Accordingly, in some embodiments, the wearable device 40 may provide a control indication (e.g., an electric voltage or current supplied by the controller 502, power source 504, electrode, and/or other electrical device) to cause the first independent foot stimulation section 701 and the second independent foot stimulation section 703 to provide an amount of stimulation (e.g., compression force) corresponding with the detected amount of applied pressure in each of the first foot zone 704 and second foot zone 706. In some examples, a stimulation protocol may be based at least in part on the user's current activity. By way of example, the amount of stimulation provided by the first independent foot stimulation section 701 (e.g., 90% stimulation) may correspond with a detected amount of pressure (e.g., 90% pressure) in the first foot zone 704. Similarly, the amount of stimulation provided by the second independent foot stimulation section 703 (e.g., 75% stimulation) may correspond with a detected amount of pressure (e.g., 75% pressure) in the first foot zone 704. Additionally, the range of pressure that can be provided by a particular independent foot stimulation section may be associated with a particular voltage output range (e.g., 0V may be associated with 0% pressure, 5V may be associated with 50% pressure and 10V may be associated with 100% pressure). Thus, an amount of compression force provided may correspond with a stimulation amount/corresponding voltage. In some embodiments, more stimulation may be provided by certain foot zones in response to detecting a particular type of terrain. For example, more stimulation may be provided to a lower foot zone when on an incline and more stimulation may be provided to an upper foot zone during declination. Accordingly, a stimulation amount may be linearly synchronized with a detected amount of pressure.

In some embodiments, a wearable device 40 may be used in conjunction with a prosthetic limb. In such examples, positioning sensors may be utilized to provide additional information/data relating to user balance information. By way of example, a perpendicular position of an example prosthetic foot may correspond with a 0V output. In such examples, the wearable device 40 may be utilized to transition a wearer to a prosthetic limb by providing stimulation/new sensations in association therewith.

Returning to FIG. 5, in certain embodiments, the controller 502 of the wearable device 40 may be configured to locally execute various algorithms on at least a portion of the raw and/or processed information/data obtained by the wearable device 40. For example, the controller 502 of the wearable device 40 may be configured to generate a movement prediction profile with respect to a wearer (e.g., in conjunction with one or more onboard sensors). In other embodiments, the controller 502 of the wearable device 40 transmits data objects describing at least a portion of the raw and/or processed information/data for processing by the movement prediction computing entity 10. As part of processing the raw data received from the one or more sensors, the controller 502 of the wearable device 40 may be configured to receive data objects describing additional information (e.g., physiological data, biological data, and the like) from a user computing entity 20 and/or from the movement prediction computing entity 10. Such additional information may be utilized for determining appropriate control signals in conjunction with a stimulation protocol in order to provide stimulation/feedback. In some embodiments, the controller 502 of the wearable device 40 may be configured to transmit (periodically or on request) data objects describing at least a portion of the raw data to the movement prediction computing entity 10 for processing. The controller 502 of the wearable device 40 may be configured to obtain (e.g., request and receive) a movement prediction profile data object (e.g., comprising stimulation protocols for a plurality of different user states) from the movement prediction computing entity 10 and store the movement prediction profile data object. The controller 502 of the wearable device 40 may cause one or more independent foot stimulation sections to provide stimulation based at least in part on a determination that the user's current state satisfies particular criteria associated with a stimulation protocol. In some embodiments, the wearable device 40 comprises a power source 504 (e.g., one or more batteries) to provide power to the onboard controller 502 (e.g., and, in some examples, an electrode, a current generator or circuit operatively coupled to the plurality of independent foot stimulation sections of the wearable device 40).

In various embodiments, each of the elements of the wearable device 40 (e.g., the first independent foot stimulation section 501, the second independent foot stimulation section 503, the third independent foot stimulation section 505, the controller 502, the power source 504 and at least one IMU 506) is in electronic communication with the wearable device 40 such that it can exchange information/data (e.g., receive and transmit data, data objects and the like) with the wearable device 40 controller 502/processor.

As discussed herein, the controller 502 may comprise one or more control elements for transmitting a control signal to control (e.g., adjust or modify) various operations and operational parameters of the wearable device 40. For example, the user may control (e.g., override) the wearable device 40, for example in order to adjust features of or stop operations of the wearable device 40. In another example, a user may transmit a control signal to adjust stimulation intensity. In some embodiments, machine learning techniques may be utilized to analyze successful guidance and/or self-adjust wearable device 40 parameters. In some embodiments, an alert may be provided to notify a user about an inferred effectiveness of the wearable device 40.

V. Exemplary System Operations

As described below, the apparatuses, systems, and methods described herein provide a robust system for providing stimulation via a wearable device. Moreover, various embodiments of the present invention disclose movement prediction machine learning models that can make inferences based at least in part on sensory data in order to perform prediction-based tasks in a more computationally efficient manner than state-of-the-art systems. Accordingly, various embodiments of the present disclosure make substantial technical contributions to the field of monitoring devices and substantially improve state-of-the-art systems.

FIG. 8, FIG. 9 and FIG. 10 are flowcharts illustrating example steps, processes, procedures, and/or operations; FIG. 11 provides an operational example of generating user interface data. Although the following exemplary operations are described as being performed by one of the wearable device 40 (e.g., via the controller 502), the movement prediction computing entity 10, or the user computing entity 20, it should be understood that in various embodiments, the operations can be interchangeably performed by other components within the system architecture 100.

Various embodiments may be configured to utilize one or more user profiles (e.g., a user-specific movement prediction profile) to facilitate operations of the wearable device 40. The user-specific movement prediction profile may comprise data indicative of features of the user (e.g., data indicative of the user's age, gender, medical conditions, and/or the like, which may be obtained from electronic medical record (EMR) data stored in a data storage area and associated with the user), as well as data indicative of functional results of operations of the wearable device (e.g., data relating to a user's historical movement information) determined based at least in part on the operation of the sensors of the wearable device 40. Accordingly, the movement prediction computing entity 10 may be configured to obtain (e.g., receive) and process data objects describing raw data (sensor data, physiological data, user profile information/data, and/or the like) associated with a user in order to generate a movement prediction profile for the user. An example movement prediction profile may comprise a plurality of movement feature sets defining a set of threshold values and/or features associated with user balance information (e.g., a particular foot position, foot pressure, foot angle, user activity, and/or the like). The movement prediction profile may be stored in conjunction with or otherwise associated with a user profile data object. The movement prediction computing entity 10 may be configured to generate or identify, based at least in part on the movement prediction profile and user profile information, a plurality of movement feature sets each corresponding with an activity type and user balance information for the user. Additionally, a movement prediction profile may comprise a plurality of stimulation protocols that are each associated with a movement feature set. Each stimulation protocol may define one or more electrical pulses (e.g., a sequence of electrical pulses) that are associated with a target foot zone and/or at least one of a plurality of independent stimulation sections of a wearable device. Each electrical pulse may be defined by one or more characteristics (i.e., electrical pulse characteristics) including, without limitation, intensity (e.g., defined by amplitude, voltage and/or current characteristics), duration (e.g., pulse duration), wave type and/or wave form. A stimulation protocol may be triggered/initiated in response to detecting one or more movement characteristics associated with a user of a wearable device that are in turn associated with a particular movement feature set. In various embodiments, a stimulation protocol may be delivered to at least one target foot zone via one or more independent stimulation sections positioned adjacent the at least one target foot zone.

A movement prediction profile data object may be stored in conjunction with or otherwise associated with a user profile data object. In some embodiments, an operator (e.g., a clinician or the wearer) interfacing with the movement prediction computing entity 10 may modify the movement prediction profile data object and/or stimulation protocols associated with the movement prediction profile data object. The movement prediction computing entity 10 may be configured to store and/or in turn provide (e.g., send, transmit) the movement prediction profile data object and the stored stimulation protocols to the wearable device 40. The movement prediction computing entity 10 may be configured to obtain (e.g., receive, request) and process a data object describing raw data (e.g., sensor data) collected by sensors of the wearable device 40 (e.g., one or more tactile pressure sensors or IMUs) and/or other sensors and sensing devices associated with the user in order to update the movement prediction profile data object and the stored stimulation protocols for the user. The movement prediction computing entity 10 may be configured to process (periodically or in response to receiving particular data) additional data/information associated with the user in order to update (e.g., adjust, change) the movement prediction profile data object and/or stored stimulation protocols for the user. The movement prediction computing entity 10 may periodically provide (e.g., send, transmit) an up-to-date movement prediction profile and stimulation protocols to the wearable device 40. The movement prediction computing entity 10 may generate a user interface data object corresponding with the movement prediction profile data object and provide (e.g., transmit, send, and/or the like) the user interface data object to one or more a user computing entities 20 or other computing entities (e.g., other computing entities operated by the user, clinicians and/or the like) for presentation by the noted computing entities.

Exemplary Techniques for Generating a Movement Prediction Profile

In various embodiments, an example wearable device 40 may be configured to generate a movement prediction profile. In various embodiments, a wearable device 40 may be configured to store a movement prediction profile defining a plurality of movement feature sets. The movement prediction profile may be utilized to identify user balance/movement characteristics in addition to a corresponding stimulation protocol.

A movement prediction profile may differ between individual users. For example, a standing (e.g., neutral) foot pressure distribution may be different for a first user and second user. Similarly the first user's gait (and corresponding foot pressure distributions, foot positions and foot angles) may be different from that of the second user. Accordingly, the movement feature sets may differ based at least in part on unique features of each individual user. The wearable device 40 may be configured to generate a movement prediction profile based at least in part on sensor data collected in real-time from one or more sensors of the wearable device. In an instance in which one or more features correspond with a movement feature set or satisfy a movement feature set threshold (e.g., by satisfying one or more foot pressure values for each of a plurality of foot zones), the wearable device 40 may identify and initiate a corresponding stimulation protocol. For example, a stimulation protocol for a standing position in which a user has both feet placed firmly on the ground may comprise providing no stimulation (e.g., 0V). In another example, a stimulation protocol for a walking stride in which a front portion of a user's right foot is in contact with the ground while a back portion of the right foot is in the air may comprise providing stimulation to one or more target foot zones associated with the front portion of the right foot. Additionally, if the user's left foot is firmly on the ground, the stimulation protocol may also comprise providing no stimulation to the user's left foot. Accordingly, while a user is walking within a particular environment/terrain, a wearable device may provide stimulation (e.g., electrical pulses) to one or more target foot zones based at least in part on a current location/position of the user's foot relative to the ground. Determining whether a movement feature set threshold is satisfied for a particular user may be based at least in part on features of the user, features of the user's current activity, data indicative of the user's current location, and/or the like.

Referring now to FIG. 8, a flowchart diagram illustrating an example process 800 for generating a movement prediction profile by a movement prediction computing entity 10 (or wearable device 40) in accordance with some embodiments of the present disclosure is provided.

Beginning at step/operation 802, movement prediction computing entity 10 obtains an event data object. The event data object may be a data object storing and/or providing access to information/data that is related a user of a wearable device, in particular user balance and/or user movement information. In some embodiments, an event data object may describe one or more recorded events associated with a user of a wearable device. In some embodiments, the event data object may comprise sensor data (e.g., foot pressure distribution information/data, foot position and foot angle information/data, location information/data, and/or the like) associated with a user's foot/feet, the user's movements and the user's environment. In some embodiments, the event data object may be provided by a wearable device 40 in electronic communication with the movement prediction computing entity 10.

Subsequent to step/operation 802, the process 800 proceeds to step/operation 804. At step/operation 804, movement prediction computing entity 10 identifies based at least in part on analysis of the event data object, one or more movement characteristics (e.g., foot pressure distributions, foot angles, and/or foot positions) associated with a particular user state and/or user environment.

Subsequent to step/operation 804, the process 800 proceeds to step/operation 806. At step/operation 806, movement prediction computing entity 10 generates, using a movement prediction machine learning model, a movement prediction profile based at least in part on the one or more movement characteristics. For example, the movement prediction computing entity 10 may identify a plurality of movement feature sets defining one or more movement characteristics associated with each user state and/or user environment. By way of example, a movement feature set may be or comprise a gradient representation of pressure distribution across at least a portion of a user's foot. For instance, a first movement feature set (e.g., foot pressure distribution) may be associated with a user's standing position when both feet are in contact with the ground. In another example, a second movement feature set may be associated with a user's walking stride. The movement prediction profile machine learning model may refer to a data object that describes steps/operations, hyper-parameters, and/or parameters of a machine learning model/algorithm that is configured to generate data needed to infer/generate a movement profile with respect to a person (e.g., a user of a wearable device). The steps/operations of the movement prediction machine learning model may lead to performing one or more prediction-based tasks (e.g., providing the movement prediction profile for use in conjunction with a wearable device in order to provide stimulation while a user is walking). In some embodiments, the movement prediction machine learning model may comprise a first sub-model that is configured to generate a movement prediction profile comprising one or more movement feature sets. In some embodiments, the movement prediction machine learning model may comprise a second sub-model that is configured to generate a plurality of stimulation protocols that are each associated with a particular movement feature set. The movement prediction machine learning model may be trained based at least in part on a ground truth event data object (e.g., describing user-specific data). By way of example, the movement prediction machine learning model/algorithm may be a neural network, a convolutional neural network (CNN), a recurrent neural network (RNN), and/or the like.

Subsequent to step/operation 806, at step/operation 808, movement prediction computing entity 10 performs one or more prediction-based tasks. As noted above, the one or more prediction-based tasks may comprise providing the movement prediction profile for use in conjunction with a wearable device 40 in order to provide stimulation to a wearer.

Exemplary Wearable Device Operations

Referring now to FIG. 9, a flowchart diagram illustrating an example process 900 performed by a wearable device 40 in accordance with some embodiments of the present disclosure is provided.

Beginning at step/operation 902, the controller 502 of the wearable device 40 may be configured to generate an event data object for a wearer of the wearable device 40. The event data object may be a data object storing and/or providing access to information/data with respect to a user of a wearable device. In some embodiments, an event data object may describe one or more recorded events that have been recorded to have occurred in relation to a user of a wearable device. In some embodiments, the event data object may comprise sensor data associated with user balance information and/or movement information.

Subsequent to generating the event data object at step/operation 902, at step/operation 904, the controller 502 of the wearable device 40 provides the event data object to the movement prediction computing entity 10. In some embodiments, the controller 502 of the wearable device 40 may obtain (e.g., collect) user sensor data via one or more sensors (e.g., IMUs, tactile pressure sensors, and/or the like) of a wearable device 40 for an initial time period and generate and transmit a user sensor data object describing at least a portion of the obtained user sensor data to the movement prediction computing entity 10.

At step/operation 906, the controller 502 of the wearable device obtains (e.g., requests, receives, or the like) a movement prediction profile data object comprising stimulation protocols from the movement prediction computing entity 10. The controller 502 of the wearable device 40 may, in certain embodiments, receive an applicable stored user profile for a user based at least in part on user input received via a user interface of the wearable device 40 (or based at least in part on user input data received from a user computing entity associated with the wearable device 40). It should be understood that an appropriate user profile data object may be identified via any of a variety of alternative mechanisms, such as by identifying a user profile associated with a particular user computing entity (e.g., the user profile of a designated owner of a user computing entity) that is within communication range of the wearable device 40. In some embodiments, the wearable device 40 may request the user profile data object from the movement prediction computing entity 10. The controller 502 of the wearable device 40 may periodically request an updated movement prediction profile data object for the wearer of the wearable device 40 from the movement prediction computing entity 10. In some embodiments, the controller 502 of the wearable device 40 may generate at least a portion of data stored within the movement prediction profile data object. In one example, the controller of the wearable device 40 may generate an initial movement prediction profile data object for a user based at least in part on evaluation of user sensor data collected via one or more sensors of the wearable device 40 while the user is wearing the wearable device 40. In some embodiments, the wearable device 40 may determine initial operating parameters and/or generate a movement prediction profile data object by monitoring the user (e.g., obtaining and analyzing sensor data collected via one or more sensors of the wearable device 40 for an initial time period). In some embodiments, the wearable device 40 may provide (e.g., transmit, send) an event data object to the movement prediction computing entity 10 for generating and storing the movement prediction profile data object within a data storage area associated with the movement prediction computing entity 10. Subsequent to periodically receiving new information and/or data, the wearable device 40 or movement prediction computing entity 10 may update the movement prediction profile data object stored in conjunction with a user profile data object and provide (e.g., transmit) an updated movement prediction profile data object periodically and/or on request.

Subsequent to obtaining a movement prediction profile data object at step/operation 906, at step/operation 908, the controller 502 of the wearable device 40 provides stimulation (e.g., via a plurality of independent foot stimulation sections) based at least in part on the movement prediction profile data object and stimulation protocols associated therewith. For example, the wearable device 40 may identify a threshold number of features from a movement feature set associated with real-time movement characteristics detected via one or more onboard sensors of the wearable device 40. In some embodiments, the controller 502 of the wearable device 40 analyzes at least a portion of sensor data collected by one or more sensors of the wearable device 40 in order to identify one or more movement features. The wearable device 40 may store at least a portion of the sensor data and/or results of the analysis in conjunction with the movement prediction profile data object. The wearable device 40 may store the sensor data in association with sensor identifier information/data (e.g., metadata, timestamp data and/or the like).

Exemplary Techniques for Updating a Movement Prediction Profile

Referring now to FIG. 10, a flowchart diagram illustrating an example process 1000 for providing an updated movement prediction profile data object by a movement prediction computing entity 10 or another computing entity, in accordance with some embodiments of the present disclosure is provided.

Beginning at step/operation 1002, the movement prediction computing entity 10 obtains (e.g., receives) the event data object (e.g., from the wearable device 40).

Subsequent to obtaining the event data object at step/operation 1002, at step/operation 1004, the movement prediction computing entity 10 obtains a user profile data object describing user information/data. In some embodiments, the user profile data object may be provided by a remote computing entity (e.g., a remote computing entity storing user EMR data). The user profile data object may describe various types of information associated with a particular user including, but not limited to, age, gender, weight, height, body mass index (BMI), weight distribution and/or the like. In some embodiments, user profile data objects describing user information may be provided by one or more computing entities, one or more other wearable or health management devices (e.g., fitness trackers), a mobile device and/or the like. In some embodiments, step/operation 1004 may be performed as part of registering a user. For example, a user profile data object for a user may be generated/created as part of registration. However, as will be recognized, a user profile may already exist and be stored in a user profile database. In such a case, registration may link the user to an existing user profile. Each user profile may be identifiable via one or more identifiers (e.g., social security numbers, patient IDs, member IDs, participant IDs, usernames, one or more globally unique identifiers (GUIDs), universally unique identifiers (UUIDs), and/or the like) that are configured to uniquely identify the user profile. As part of registering a user, movement prediction computing entity 10 may obtain (e.g., request and receive) various data objects describing information/data associated with a user. In various embodiments, movement prediction computing entity 10 receives one or more data objects describing the user information/data for generation/creation of and/or storage in conjunction with a user profile data object. In some embodiments, a user's EMR may be associated with and/or otherwise stored in conjunction with the user profile data object. The movement prediction computing entity 10 may store the event data object in conjunction with the user profile data object.

Subsequent to obtaining the user profile data object at step/operation 1004, at step/operation 1006, based at least in part on the user information stored in a user profile data object and the event data object associated therewith, the movement prediction computing entity 10 determines a plurality of stimulation protocols where each stimulation protocol is associated with a particular movement feature set. The movement feature set may be a set of values/amounts such as foot angle, foot position and foot pressure distribution values. The movement feature set may be influenced by and determined based at least in part on additional user parameters (e.g., age, gender, body weight, height, historical movement information/data, and/or the like).

Subsequent to determining a plurality of stimulation protocols at step/operation 1006, at step/operation 1008, the movement prediction computing entity generates a movement prediction profile data object. The movement prediction computing entity 10 may be configured to periodically update the movement prediction profile data object as additional data for the user (e.g., changes in the user profile data object) is obtained so as to maintain an updated movement prediction profile data object for the user. In some embodiments, the wearable device 40 may be configured to determine the movement prediction profile data object for a user and provide (e.g., transmit, send) the movement prediction profile data object to the movement prediction computing entity 10.

Subsequent to generating a movement prediction profile data object at step/operation 1008, at step/operation 1010, the movement prediction computing entity 10 stores the movement prediction profile data object in association with the user profile data object. As noted, the movement prediction profile data object for a user may be periodically updated (e.g., as new data is provided to a user's EMR, as the wearable device 40 is utilized over time, and/or the like). Accordingly, the controller 502 may implement a feedback loop that updates the movement prediction profile data object for a user based at least in part on a determined accuracy relating to effectiveness of stimulation protocols and/or user provided input. For example, the movement prediction computing entity 10 may determine whether a duration or intensity of an electrical pulse should be increased or decreased based at least in part on whether the user indicates that the stimulation provided was adequate or whether the user's overall amount of movement is increasing or decreasing over time. For example, if a user progressively takes fewer steps or walks less over a time period (e.g., one week) the movement prediction computing entity may determine that the stimulation being provided is inadequate and may increase the intensity and/or duration of electrical pulses associated with the plurality stimulation protocols for the user to provide increased stimulation and encourage the user to move/walk more frequently.

Subsequent to storing the movement prediction profile data object at step/operation 1010, at step/operation 1012, the movement prediction computing entity 10 provides (e.g., transmits, sends and/or the like) the movement prediction profile data object to the controller 502 of the wearable device 40 to facilitate operations.

At step/operation 1014, movement prediction computing entity 10 periodically obtains an updated movement prediction profile data object describing user information and/or sensor data obtained by controller 502 of the wearable device 40 including, e.g., user response data, biometric data, and/or the like.

Subsequent to step/operation 1014, at step/operation 1016, in response to receiving an updated user profile data object, the movement prediction computing entity 10 updates the movement prediction profile data object and/or stimulation protocols for the user which are stored in conjunction with user profile data object. The movement prediction computing entity 10 may update the movement prediction profile data object and/or stimulation protocols based at least in part on new user EMR data, biometric data and/or sensor data provided by other computing entities and/or the like. In so doing, the movement prediction computing entity 10 can refine the outputs generated by the wearable device 40 over time and provide more effective stimulation. Additionally, the most effective stimulation protocols for a particular user, and for particular population subgroups sharing certain characteristics (e.g., age, weight, gender, known health conditions) can be identified over time. In certain embodiments, the movement prediction computing entity 10 may be configured to refine one or more stimulation protocols for a user using a movement prediction machine learning model (e.g., a trained neural network). Moreover, updated information based at least in part on new user features (e.g., weight loss or weight gain, medical history including recent medical procedures and/or the like) can be provided for updating the movement prediction profile data object, which may be utilized to refine stimulation protocols to be utilized for certain population subgroups. In some embodiments, the user computing entity 20 and/or one or more other computing devices may be are configured to obtain (e.g., monitor, detect, and/or the like) additional body data and provide data object(s) associated therewith. The body data may be or comprise physiological information/data, biometric information/data, heart rate data, oxygen saturation data, pulse rate data, body temperature data, breath rate data, perspiration data, blood pressure data, neural activity data, cardiovascular data, pulmonary data, and/or various other types of information/data which may be relevant for updating the movement prediction profile data object storing the plurality of stimulation protocols for a user.

Subsequent to updating the user profile data object at step/operation 1016, at step/operation 1018, the movement prediction computing entity 10 transmits an updated movement prediction profile data object to the wearable device 40. In various embodiments, the movement prediction computing entity 10 and the wearable device 40 periodically update and provide (e.g., send, transmit) movement prediction profile data objects and in so doing effectively incorporate real-time user information and user profile information/data in a continuous feedback loop.

Exemplary Techniques for Generating User Interface Data

In various embodiments, a variety of sources (e.g., movement prediction computing entity 10) may provide (e.g., transmit, send) a mobile application for download and execution on a user computing entity 20 (e.g., in response to a request to download the mobile application generated at the user computing entity 20). In another embodiment, the mobile application may be pre-installed on the user computing entity 20. And in yet another embodiment, the mobile application may be a browser executing on the user computing entity 20. The mobile application may comprise computer-executable program code (e.g., a software application) that provides the functionality described herein. The mobile application may enable various functionalities as discussed herein. Moreover, although specifically referenced as a mobile application, it should be understood that the mobile application may be executable by any of a variety of computing entity types, such as desktop computers, laptop computers, mobile devices, and/or the like. In various embodiments, instructions may be automatically generated (e.g., by the movement prediction computing entity 10) or provided based at least in part in response to clinician input/instructions provided by a clinician interacting with the movement prediction computing entity 10. The instructions may comprise messages in the form of banners, headers, notifications, and/or the like.

In some embodiments, at least a portion of the obtained wearable device sensor data may be transferred to the user computing entity 20 and/or the movement prediction computing entity 10 for performing at least a portion of the required operations. The wearable device 40 or user computing entity 20 may be configured to provide information/data in response to requests/queries received from the movement prediction computing entity 10. In various embodiments, the wearable device 40 may be managed, calibrated and/or otherwise controlled at least in part by a movement prediction computing entity 10. The movement prediction computing entity 10 may generate a user interface data object based at least in part on a user profile data object and provide (e.g., transmit, send) the user interface data object to one or more client computing entities.

FIG. 11 provides an operational example of a user interface that may be described by a user interface data object generated by the movement prediction computing entity 10. The movement prediction computing entity 10 may generate an alert or notification based at least in part on data/information stored in association with a user profile data object. The wearable device 40/movement prediction computing entity 10 may provide one or more data objects corresponding with the alert/notification for presentation by a user computing entity 20 (e.g., for dynamically updating a user interface 1102 of a user computing entity 20). In one example, as depicted, the user interface 1102 of the user computing entity 20 provides an alert for the user to provide input regarding the functioning of the wearable device 40. As depicted, the user interface 1102 depicts a plurality of user-selectable user interface data objects that allow a user to indicate whether he or she would like an increase in stimulation, a decrease in stimulation or no change to stimulation being provided. Additionally, in some examples, the user interface 1102 may provide information regarding a total number of steps taken over a time period (e.g., daily, weekly) in order to encourage the user to be more active/take more steps.

As will be recognized, a variety of other approaches and techniques can be used to adapt to various needs and circumstances. The present disclosure provides techniques that assist with mobility by confirming proper foot placement based at least in part on provided stimulation/feedback to an area of the body. As a result, this keeps the wearer walking and moving, also preventing potential detrimental complications that immobility and, in particular, progressive peripheral neuropathy can cause. This technology can prevent ankle and leg injuries resulting from decreased nervous system function and provide a wearer with additional security and comfort regarding foot placement while going about daily activities. Long-term, the techniques discussed herein can extend a wearer's life and prevent more detrimental additive complications by assisting mobility.

Accordingly, as described above, the apparatuses, systems, and methods described herein provide a robust movement detection and stimulation system. Moreover, various embodiments of the present invention disclose movement prediction machine learning models that can make inferences based at least in part on sensory data in order to provide more effective stimulation compared to the state-of-the-art systems. Accordingly, various embodiments of the present disclosure make substantial technical contributions to the field of monitoring devices and substantially improve state-of-the-art systems.

VI. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only, and not for purposes of limitation.

The invention claimed is:

1. A computer-implemented method comprising:
   identifying, by one or more processors and based at least in part on an event data object that comprises sensor data describing user movement information associated with at least one foot of a user, one or more movement characteristics associated with the user;
   determining, by the one or more processors, based at least in part on the one or more movement characteristics and using a movement prediction machine learning model, a movement prediction profile that comprises a plurality of movement feature sets associated with the at least one foot of the user, wherein:
   (i) each movement feature set of the plurality of movement feature sets is associated with a respective stimulation protocol of a plurality of stimulation protocols, and
   (ii) each stimulation protocol of the plurality of stimulation protocols is associated with one or more target stimulation zones; and
   initiating, by the one or more processors, stimulation output to one or more electroactive polymers associated with the one or more target stimulation zones based at least in part on one or more stimulation protocols of the plurality of stimulation protocols for the one or more target stimulation zones as indicated by the movement prediction profile provided by the movement prediction machine learning model.

2. The computer-implemented method of claim 1, further comprising:
   providing, by the one or more processors, a movement prediction profile data object to a user computing entity; and
   storing, by the one or more processors, information associated with the movement prediction profile to a user profile.

3. The computer-implemented method of claim 1, wherein the sensor data is captured in real time by at least one sensor of a wearable device.

4. The computer-implemented method of claim 3, wherein the at least one sensor comprises one or more of a tactile pressure sensor or an inertial measurement unit (IMU).

5. The computer-implemented method of claim 1, further comprising:
   storing the movement prediction profile for the user comprising (a) the plurality of movement feature sets, and (b) the plurality of stimulation protocols each corresponding with a particular movement feature set of the plurality of movement feature sets, wherein each movement feature set of the plurality of movement feature sets describes a gradient representation of pressure distribution across at least a portion of the at least one foot of the user.

6. The computer-implemented method of claim 1, wherein:
   at least one wearable knee brace comprises the one or more electroactive polymers.

7. The computer-implemented method of claim 1, further comprising:
   storing a subset of the sensor data; and
   transmitting at least the subset of the sensor data to a computing entity that is in communication with a wearable device.

8. The computer-implemented method of claim 1, wherein each movement feature set of the plurality of movement feature sets comprises one or more of user balance information or environmental information.

9. The computer-implemented method of claim 1, wherein the movement prediction machine learning model comprises a trained neural network.

10. The computer-implemented method of claim 1, wherein each of the plurality of stimulation protocols is associated with an electrical pulse intensity and an electrical pulse duration.

11. A system comprising memory and one or more processors communicatively coupled to the memory, the one or more processors configured to:
    identify, based at least in part on an event data object that comprises sensor data describing user movement information associated with at least one foot of a user, one or more movement characteristics associated with the user;
    determine, based at least in part on the one or more movement characteristics and using a movement prediction machine learning model, a movement prediction profile that comprises a plurality of movement feature sets associated with the at least one foot of the user, wherein:
    (i) each movement feature set of the plurality of movement feature sets is associated with a respective stimulation protocol of a plurality of stimulation protocols, and
    (ii) each stimulation protocol of the plurality of stimulation protocols is associated with one or more target stimulation zones; and
    initiate stimulation output to one or more electroactive polymers associated with the one or more target stimulation zones based at least in part on one or more stimulation protocols of the plurality of stimulation protocols for the one or more target stimulation zones as indicated by the movement prediction profile provided by the movement prediction machine learning model.

12. The system of claim 11, wherein the one or more processors are further configured to:
provide a movement prediction profile data object to a user computing entity; and
store information associated with the movement prediction profile to a user profile.

13. The system of claim 11, wherein the sensor data is captured in real time by at least one sensor of a wearable device.

14. The system of claim 11, wherein each movement feature set of the plurality of movement feature sets comprises one or more of user balance information or environmental information.

15. The system of claim 11, wherein the movement prediction machine learning model comprises a trained neural network.

16. One or more non-transitory computer-readable storage media including instructions that, when executed by one or more processors, cause the one or more processors to:
identify, based at least in part on an event data object that comprises sensor data describing user movement information associated with at least one foot of a user, one or more movement characteristics associated with the user;
determine, based at least in part on the one or more movement characteristics and using a movement prediction machine learning model, a movement prediction profile that comprises a plurality of movement feature sets associated with the at least one foot of the user, wherein:
 (i) each movement feature set of the plurality of movement feature sets is associated with a respective stimulation protocol of a plurality of stimulation protocols, and
 (ii) each stimulation protocol of the plurality of stimulation protocols is associated with one or more target stimulation zones; and
initiate stimulation output to one or more electroactive polymers associated with the one or more target stimulation zones based at least in part on one or more stimulation protocols of the plurality of stimulation protocols for the one or more target stimulation zones as indicated by the movement prediction profile provided by the movement prediction machine learning model.

17. The one or more non-transitory computer-readable storage media of claim 16, wherein the instructions, when executed by the one or more processors, further cause the one or more processors to:
provide a movement prediction profile data object to a user computing entity; and
store information associated with the movement prediction profile to a user profile.

18. The one or more non-transitory computer-readable storage media of claim 16, wherein the sensor data is captured in real time by at least one sensor of a wearable device.

19. The one or more non-transitory computer-readable storage media of claim 16, wherein each movement feature set of the plurality of movement feature sets comprises one or more of user balance information and environmental information.

20. The one or more non-transitory computer-readable storage media of claim 16, wherein the movement prediction machine learning model comprises a trained neural network.

* * * * *